United States Patent
Padrela et al.

(10) Patent No.: US 12,357,574 B2
(45) Date of Patent: Jul. 15, 2025

(54) PARTICLE COATING METHOD

(71) Applicant: University of Limerick, Limerick (IE)

(72) Inventors: Luis Padrela, Limerick (IE); Vivek Verma, Limerick (IE); Kevin Ryan, Limerick (IE)

(73) Assignee: University of Limerick, Limerick (IE)

( * ) Notice: Subject to any disclaimer, the term of this patent is extended or adjusted under 35 U.S.C. 154(b) by 7 days.

(21) Appl. No.: 17/904,511

(22) PCT Filed: Feb. 19, 2021

(86) PCT No.: PCT/EP2021/054235
§ 371 (c)(1),
(2) Date: Aug. 18, 2022

(87) PCT Pub. No.: WO2021/165514
PCT Pub. Date: Aug. 26, 2021

(65) Prior Publication Data
US 2023/0111202 A1    Apr. 13, 2023

(30) Foreign Application Priority Data

Feb. 19, 2020  (EP) .................................... 20158366
Jul. 6, 2020   (GB) .................................... 2010362

(51) Int. Cl.
*A61K 9/16*     (2006.01)
*A61K 31/192*   (2006.01)
(Continued)

(52) U.S. Cl.
CPC .......... *A61K 9/1682* (2013.01); *A61K 9/1676* (2013.01); *A61K 31/192* (2013.01);
(Continued)

(58) Field of Classification Search
None
See application file for complete search history.

(56) References Cited

U.S. PATENT DOCUMENTS

2003/0215572 A1   11/2003  Nojiri et al.
2006/0039983 A1*  2/2006   Shekunov ............ A61K 9/1694
                                                          424/489
(Continued)

FOREIGN PATENT DOCUMENTS

JP    H1129717 A      2/1999
KR    20160097765 A   8/2016
(Continued)

OTHER PUBLICATIONS

International Search Report and Written Opinion for PCT/EP2021/054235 issued May 19, 2021, 11 pages.

*Primary Examiner* — Shamim Ahmed
*Assistant Examiner* — Bradford M Gates
(74) *Attorney, Agent, or Firm* — Husch Blackwell LLP

(57) ABSTRACT

A method of producing a particle coating on one or more items is provided. The method comprises mixing supercritical carbon dioxide with a solution comprising dissolved material for forming particles. The method further comprises spraying the mixture into a precipitation chamber (316) to precipitate particles, wherein the chamber is at a pressure below a supercritical pressure of the supercritical fluid. The method also comprises capturing the precipitated particles on one or more items located within the chamber.

18 Claims, 17 Drawing Sheets

(51) Int. Cl.
     *A61K 31/519*     (2006.01)
     *A61K 31/549*     (2006.01)
     *A61K 31/55*      (2006.01)
     *B05D 1/12*       (2006.01)

(52) U.S. Cl.
     CPC .......... *A61K 31/519* (2013.01); *A61K 31/549* (2013.01); *A61K 31/55* (2013.01); *B05D 1/12* (2013.01)

(56) References Cited

U.S. PATENT DOCUMENTS

| | | | |
|---|---|---|---|
| 2006/0210640 A1 | 9/2006 | Kerkhof | |
| 2015/0000846 A1 | 1/2015 | Risse et al. | |
| 2016/0346206 A1 | 12/2016 | Costa et al. | |
| 2018/0062155 A1* | 3/2018 | Mitchell | B01J 8/386 |
| 2019/0016962 A1* | 1/2019 | Gupta | B01F 33/404 |

FOREIGN PATENT DOCUMENTS

| | | | |
|---|---|---|---|
| WO | 2004091571 A2 | 10/2004 | |
| WO | 2015053857 A3 | 6/2015 | |
| WO | 2016156841 A1 | 10/2016 | |

\* cited by examiner

A1

A2

C1

C2

PARTICLE COATING METHOD

FIELD OF THE INVENTION

The present invention relates to a method for producing a particle coating on one or more items, and in particular but not exclusively for producing a nanoparticle coating on carrier particles.

BACKGROUND

Particles such as nanoparticles of active pharmaceutical ingredients (API) provide advantageous properties such as improved solubility, dissolution rate and bioavailability when compared to conventional larger API particles. However, particles such as nanoparticles are not readily produced, stabilized and isolated using conventional techniques. Where further reduction of API nanoparticle size below 500 nm is required, that typically compromises the physiochemical properties of the API nanoparticles (including rheological properties such as flowability and compressibility).

Top down techniques for generating nanoparticles include milling and high-pressure homogenisation, while bottom-up techniques include liquid and supercritical anti-solvent precipitation, and conventional nano-spray drying (for example using nitrogen). However, existing techniques for isolating API nanoparticles by coating onto carrier particles are limited in terms of controlling characteristics such as API particle size precipitated onto the carrier particles, agglomeration of API particles coated onto the carrier particles, API particle solid-state (amorphous or crystalline), API particle loading into or onto carrier particles, and low product yield due to inefficient collection of the API particles.

In particular, the supercritical anti-solvent (SAS) technique has emerged as a potential technique to produce API nanoparticles with controlled particle shape and particle size distribution. The API nanoparticles may be coated onto carrier particles located inside a pressurized drying chamber. However, this process requires high pressure inside the drying chamber which limits its scalability and jeopardizes safety of the process.

The present invention has been devised with the foregoing in mind.

SUMMARY

According to a first aspect, there is provided a method of producing a particle coating on one or more items. The method may comprise mixing a supercritical fluid such as supercritical carbon dioxide with a solution comprising material such as dissolved material for forming particles. The method may also comprise spraying the formed mixture into a precipitation chamber to precipitate particles. The chamber may be at a pressure below a supercritical pressure of the supercritical fluid (below a threshold pressure required to maintain the supercritical fluid in a supercritical state). The chamber may be at substantially atmospheric pressure. The method may comprise capturing the precipitated particles on one or more items located within the chamber.

Mixing a supercritical fluid such as supercritical carbon dioxide with a solution comprising dissolved material for producing particles prior to introducing the formed mixture to a precipitation chamber may allow the chamber to be held at a pressure below a threshold pressure required to maintain the supercritical fluid in a supercritical state (for example, at atmospheric pressure). The supercritical fluid in the mixture may act as either or both of a supercritical anti-solvent and an atomization enhancer. A rapid pressure drop as the mixture is sprayed into the chamber may cause droplets of the solution to be formed as the supercritical fluid depressurizes. Due to the below supercritical pressure (for example, atmospheric pressure) in the chamber, the droplets may then rapidly dry (for example, prior to contacting the one or more items within the chamber) to form particles. The pressure (for example, atmospheric pressure) of the chamber may therefore provide a dual effect in aiding the precipitation of particles.

Previous approaches employing a supercritical anti-solvent process often require a high pressure environment to produce particles. Typically, a solution comprising dissolved material for forming particles is introduced to a chamber that already contains supercritical fluid. That requires the chamber to be sufficiently pressurized to maintain the supercritical fluid in a supercritical state. Maintaining a high pressure environment requires specialized high pressure equipment, which increases equipment costs and jeopardizes scalability and process safety. Alternative previous approaches include dissolving the material for producing particles directly into supercritical carbon dioxide and using a low pressure chamber to precipitate particles (known as rapid expansion of supercritical solution, or RESS). However, solubility in supercritical fluid such as supercritical carbon dioxide is very low for some materials. That limits the applicability of RESS processes, as the throughput is low and the process must be carried out for a longer time.

By mixing supercritical fluid such as supercritical carbon dioxide with a solution comprising dissolved material for forming nanoparticles prior to introducing the formed mixture to a precipitation chamber, precipitation of particles may be carried out below supercritical pressure of the supercritical fluid (for example, at atmospheric pressure), and cost and complexity of the process and equipment may be reduced. An advantage of atmospheric pressure may be that no specialist equipment (for example pumps) for pressurizing or providing a vacuum within the chamber is required. The chamber may also not be required to support a substantial pressure differential between an internal volume of the chamber and an external environment. In addition, the method may avoid dissolving the material for forming particles directly in supercritical fluid such as supercritical carbon dioxide, which may increase throughput and/or process efficiency.

Capturing the precipitated particles on one or more items located within the chamber soon after precipitation may reduce opportunity for the particles to agglomerate or coalesce. The particles may therefore be coated onto the one or more items substantially individually, resulting in a homogeneous particle coating. That may be particularly beneficial for nanoparticle coatings. Nanoparticles have a tendency to agglomerate which can have a deleterious effect on rheological properties of the nanoparticles such as compressibility and flowability. Integrating particle production and particle coating into a single process may avoid the need for intermediate steps to isolate the particles prior to coating (such as the use of filters or electrostatic chambers). Capturing the precipitated particles soon after precipitation may also improve the process yield (particularly in respect of nanoparticles).

The method may comprise introducing a flow of drying gas into the chamber. The supercritical anti-solvent and/or atomisation enhancement properties of supercritical fluid such as supercritical carbon dioxide may assist or enhance a spray-drying process.

The formation of droplets due to the rapid pressure drop experienced by the mixture as it passes through the nozzle means that solvent evaporation may be rapid, resulting in rapid precipitation of particles. Integrating supercritical antisolvent behaviour with a spray-drying process may further increase a rate of solvent evaporation. That may further enable particles to be rapidly produced.

Typically, spray-drying can be used to form micron sized particles (conventional spray-drying) or nanosized particles (nano spray-drying). As discussed above, nanoparticles often agglomerate if not isolated or captured on an item to be coated soon after being produced. That can result in a low processing yield for nano spray-drying, and subsequently a non-homogeneous coating on one or more coated items due to agglomerated nanoparticles. Integrating spray-drying and particle coating into a single process may improve process yield and provide a substantially homogeneous particle coating.

The method may comprise spraying the mixture through a nozzle into the precipitation chamber to precipitate particles. A particle size produced by the method may be determined or controlled by a nozzle orifice size of the nozzle (a size of one or more openings in the nozzle) through which the mixture is sprayed. Larger nozzle orifices may produce larger droplets of solution as the mixture enters the precipitation chamber, whereas smaller nozzle orifices may produce smaller droplets of solution as the mixture enters the precipitation chamber. A nozzle orifice size may be selected so as to produce nanodroplets (nanosized droplets) when spraying the mixture into the precipitation chamber, resulting in the precipitation of nanoparticles. For example, the nozzle orifice size may be substantially 150 μm or smaller to precipitate nanoparticles, and optionally may be substantially 50 μm or smaller, and further optionally may be substantially 40 μm. The particles/nanoparticles may be sized between substantially 10 nm (or 20 nm or 30 nm or 40 nm or 50 nm or 60 nm or 70 nm or 80 nm or 90 nm or 100 nm) and substantially 500 nm, and may be sized between substantially 90 nm and substantially 500 nm. Any suitable nozzle orifice size may be used to produce particles of a desired size.

The method may comprise capturing the precipitated particles on one or more items such as carrier particles in a fluidized bed located within the chamber. A fluidized bed of carrier particles may promote circulation of the precipitated particles, further enabling a homogeneous coating of particles on the carrier particles. The carrier particles may be or comprise one or more excipients. The one or more excipients may be or comprise microcrystalline cellulose. The solution may comprise an active pharmaceutical ingredient (API) or an anti-bacterial drug. The API or anti-bacterial drug may be dissolved in an organic solvent. The active pharmaceutical ingredient may be or comprise an ingredient or drug from any class (class I, class II, class III or class IV) according to the biopharmaceutical classification system (BCS). The API may be or comprise a class II or a class IV drug (according to the BCS). The active pharmaceutical ingredient may be or comprise one of carbamazepine, risperidone, ketoprofen and hydrochlorothiazide. The organic solvent may be or comprise an alcohol, for example methanol.

By selecting an appropriate nozzle orifice size, a homogeneous coating of API nanoparticles may be provided on excipient carrier particles. Providing excipient carrier particles with a homogeneous coating of individual API nanoparticles using the above method may result in coated carrier particles without requiring any additional processing steps. The coated carrier particles may have optimal rheological properties (for example, flowability or compressibility) typical of larger micron sized particles, whilst maintaining high solubility and dissolution rate profiles typical of nanosized API particles. The coated carrier particles may undergo direct compression into final oral dosage form (for example, tablet form). The method may therefore enhance the effectiveness and processability of APIs.

The method may comprise fluidizing the bed of carrier particles using the flow of drying gas. The drying gas may be or comprise one or more of carbon dioxide and nitrogen.

The method may alternatively comprise coating one or more items such as medical implants, for example joint replacement implants or stents, located within the chamber.

The method may comprise orienting the flow direction of drying gas and a spray direction of the mixture in substantially the same direction. The method may comprise directing the flow of drying gas from a top portion of the chamber towards the one or more items.

A distance between an entry location into the chamber of the spray and the one or more items may be between substantially 10 cm and substantially 20 cm, and optionally between substantially 12 cm and substantially 18 cm. The distance may be substantially 15 cm. A distance of between substantially 10 cm and substantially 20 cm may result in dry coated items with a process yield of between substantially 50% and substantially 90%. A distance between the spray entry location and the one or more items may not be less than substantially 10 cm.

The method may comprise controlling a concentration of the solution comprising dissolved material for forming particles. Controlling the concentration of the solution may enable particle loading (e.g., a mass of particle coating relative to a mass of the one or more items) on the one or more to be altered. An increased concentration of the solution may enable increased particle loading on the one or more items.

The solution may be or comprise a saturated solution. In this specification, the term 'saturated' means that a concentration of the solution is near to but not above its saturation limit. A saturated solution may enable the formation of crystalline particles. Conversely, an undersaturated solution may result in the formation of amorphous particles, whilst a supersaturated solution may result in the formation of crystalline particles but may cause blockage of the nozzle.

The method may comprise supporting the one or more items on a surface. The surface may be arranged within the chamber to allow fluid to pass through or around the surface. That may enable residual solvent or carbon dioxide or drying gas to flow to an outlet of the chamber to maintain atmospheric pressure in the chamber.

The surface may comprise a plurality of perforations or apertures to allow fluid to pass through the surface. The surface may be shaped to substantially match an internal cross-sectional shape of the chamber. The surface may be or comprise a mesh. The method may comprise selecting or controlling an area of the surface configured to allow fluid to pass through. That may enable atmospheric pressure to be maintained in the chamber. The method may comprise controlling movement of a cover disposed over the surface in order to select or control an area of the surface configured to allow fluid to pass through.

The surface may be operable within the chamber between a first position or configuration and a second position or configuration. In the first position, the surface may be configured to support the one or more items for coating. In the second position, the surface may be configured to direct or allow the coated item(s) to travel or fall towards the outlet of the chamber. The method may comprise moving the surface to the second position to remove coated items from the chamber. The method may comprise moving the surface to the first position to allow one or more uncoated items to be introduced to the chamber for coating. The method may comprise moving the surface between the first and second positions whilst spraying the mixture into the chamber substantially continuously. That may enable a semi-continuous particle coating process, by enabling coated items to be removed from the chamber (with the surface in the second position) and uncoated items to be introduced to the chamber for coating (with the surface in the first position), without stopping or interrupting spray of the mixture into the chamber. The surface may enable the mixture to be sprayed substantially continuously into the chamber in conjunction with batch insertion and extraction of items into and out of the chamber.

The method may comprise mixing the supercritical fluid such as supercritical carbon dioxide with the solution in the nozzle. The nozzle may be or comprise a high pressure nozzle. Alternatively or additionally, the nozzle may be or comprise a coaxial nozzle.

According a second aspect, there is provided a coated item such as a carrier particle comprising a homogeneous coating of particles. The item may be that discussed with respect to the first aspect. A mass of the coating of particles may be between substantially 10% of a mass of the carrier particle or greater.

The mass of the coating of particles may be substantially 15% of the mass of the carrier particle or greater, or may be substantially 20% of the mass of the carrier particle or greater, or may be substantially 25% of the mass of the carrier particle or greater.

The particles may be nanoparticles. The nanoparticles may be sized between substantially 10 nm and substantially 500 nm, and may be sized between substantially 90 nm and substantially 500 nm. Alternatively, the particles may be micron sized.

The particles (for example nanoparticles) may comprise a crystalline structure.

The particles may comprise an active pharmaceutical ingredient (API) or an anti-bacterial drug. The API may be or comprise an ingredient or drug from any class (class I, class II, class III or class IV) according to the biopharmaceutical classification system (BCS). The API may be or comprise a class II or a class IV ingredient or drug (according to the BCS). The active pharmaceutical ingredient may be or comprise one or more of carbamazepine, risperidone, ketoprofen and hydrochlorothiazide.

The carrier particle may be or comprise one or more excipients. The carrier particle may be or comprise microcrystalline cellulose.

The coated item of the second aspect may comprise one or more optional features of the method of the first aspect, and vice versa.

According to a third aspect, there is provided a method of producing particles such as nanoparticles. The method may comprise mixing a supercritical fluid such as supercritical carbon dioxide with a solution comprising material for forming particles. The method may also comprise spraying the mixture into a precipitation chamber to precipitate particles. The chamber may be at a pressure below a supercritical pressure of the supercritical fluid (for example at atmospheric pressure).

The method may comprise introducing a flow of drying gas into the chamber.

The method may comprise spraying the mixture through a nozzle into the precipitation chamber to precipitate particles. A particle size produced by the method may be determined or controlled by a nozzle orifice size of the nozzle (a size of one or more openings in the nozzle) through which the mixture is sprayed. Larger nozzle orifices may produce larger droplets of solution as the mixture enters the precipitation chamber, whereas smaller nozzle orifices may produce smaller droplets of solution as the mixture enters the precipitation chamber. A nozzle orifice size may be selected so as to produce nanodroplets (nanosized droplets) when spraying the mixture into the precipitation chamber, resulting in the precipitation of nanoparticles. For example, the nozzle orifice size may be substantially 150 μm or smaller to precipitate nanoparticles, and optionally may be substantially 50 μm or small, and further optionally may be substantially 40 μm. The nanoparticles may be sized between substantially 10 nm and substantially 500 nm, and may be sized between substantially 90 nm and substantially 500 nm. Any suitable nozzle orifice size may be used to produce particles of a desired size.

The method of the third aspect may comprise one or more optional features of the method of the first aspect or the coated item of the second aspect, and vice versa.

According to a fourth aspect, there is provided an apparatus for producing a particle coating such as a nanoparticle coating on one or more items. The apparatus may comprise a chamber and a nozzle. The nozzle may be configured to spray a mixture of supercritical fluid such as supercritical carbon dioxide and a solution comprising dissolved material for forming particles into the chamber. The chamber may be configured to be held at a pressure below a supercritical pressure of the supercritical fluid (for example at atmospheric pressure). The apparatus may comprise a surface configured to support one or more items to be coated within the chamber.

The surface may be configured to have and/or may comprise a shape which substantially matches an internal cross-sectional shape of the chamber. The surface may divide the chamber into a first portion and a second portion. The first portion may comprise the nozzle. The surface may comprise one or more apertures or perforations configured to allow fluid to pass through the surface. That may enable residual solvent or carbon dioxide to flow to an outlet of the chamber to maintain atmospheric pressure in the chamber. The outlet of the chamber may be formed in the second portion of the chamber. The surface may comprise a mesh.

The surface may comprise one or more cover portions configured to cover one or more of the apertures or perforations. The one or more cover portions may be movable with respect to the one or more apertures or perforations. The proportion of the surface configured to allow fluid to pass through may therefore be selected or controlled. That may enable the chamber to be held at atmospheric pressure during operation of the apparatus.

A distance of the surface from the nozzle may be between substantially 10 cm and substantially 20 cm, and optionally between substantially 12 cm and substantially 18 cm. The distance may be substantially 15 cm. Such distances may enable an optimal process yield.

The surface may be operable within the chamber between a first position or configuration and a second position or configuration. In the first position, the surface may be configured to support the one or more items for coating. In the second position, the surface may be configured to direct or allow the coated item(s) to travel or fall towards the outlet of the chamber. That may enable a semi-continuous particle coating process, by enabling coated items to be removed from the chamber (with the surface in the second position) and uncoated items to be introduced to the chamber for coating (with the surface in the first position), without stopping or interrupting spray of the mixture into the chamber. The surface may enable the mixture to be sprayed substantially continuously into the chamber in conjunction with batch insertion and extraction of items into and out of the chamber.

The apparatus of the fourth aspect may comprise one or more optional features of the method of the first aspect, the coated item of the second aspect and the method of the third aspect, and vice versa.

According to a fifth aspect, there is provided a surface according to the fourth aspect, the surface configured to support one or more items to be coated within a chamber.

Optional features of any of the above aspects may be combined with the features of any other aspect, in any combination. For example, features described in connection with the method of the first aspect may have corresponding features definable with respect to the coated carrier particle of the second aspect or the method of the third aspect, and these embodiments are specifically envisaged. Features which are described in the context or separate aspects and embodiments of the invention may be used together and/or be interchangeable wherever possible. Similarly, where features are, for brevity, described in the context of a single embodiment, those features may also be provided separately or in any suitable sub-combination.

BRIEF DESCRIPTION OF THE DRAWINGS

The invention will now be described by way of example with reference to the accompanying drawings in which.

Like reference numbers and designations in the various drawings may indicate like elements.

DETAILED DESCRIPTION

Figure 1:
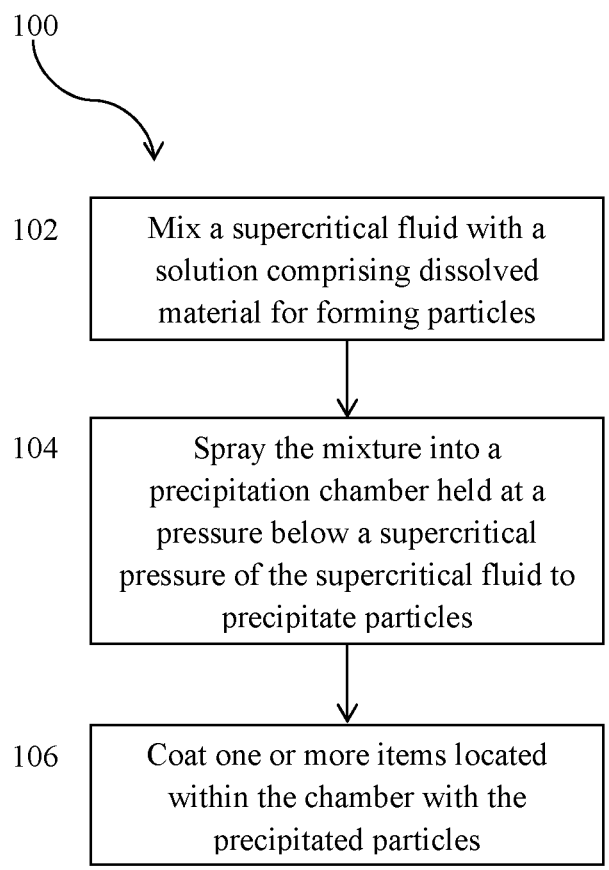
FIG. 1 shows an embodiment of a method for producing a nanoparticle coating on one or more items in accordance with the invention.

FIG. 1 shows an embodiment of a method 100 for producing a particle coating on one or more items.

The method 100 comprises mixing supercritical carbon dioxide with a solution comprising dissolved material for forming particles at step 102 (although other supercritical fluids may be used instead). The method 100 further comprises spraying the mixture into a precipitation chamber held at a pressure below a supercritical pressure of the supercritical fluid (for example, atmospheric pressure) to precipitate particles at step 104. The method 100 also comprises coating one or more items located within the chamber with the precipitated particles at step 106. The one or more items are arranged within the chamber to capture precipitated particles to form a particle coating on the one or more items.

Figure 2:
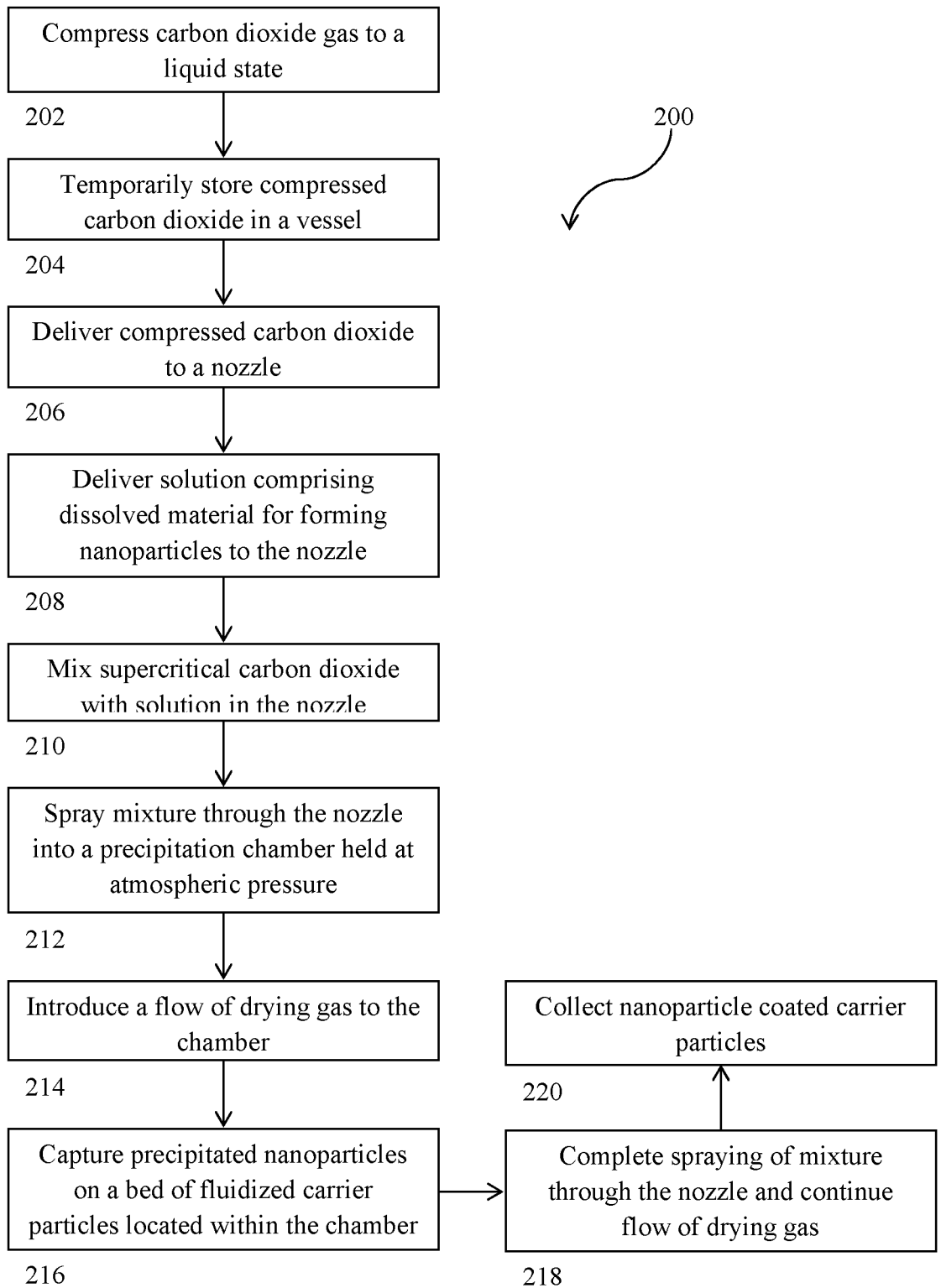
FIG. 2 shows an embodiment of a method for producing an API nanoparticle coating on carrier particles in accordance with the invention.

FIG. 2 shows an embodiment of a method 200 for producing a nanoparticle coating on one or more items, in line with the method 100 as set out above. The method 200 may be carried out using, and is described with respect to, an apparatus 300 shown in FIG. 3.

Step 202 of the method 200 comprises compressing carbon dioxide gas to a liquid state. In the embodiment shown, carbon dioxide from a cylinder 302 is compressed using a pump 304. In the embodiment shown, the pump 302 is a SFE Process Dose HPP 400-C pump, but any suitable pump may be used.

Step 204 of the method 200 comprises temporarily storing the compressed carbon dioxide in a temperature controlled vessel 306. The temperature controlled vessel 306 is stored in a temperature controlled air chamber 308. The temperature of the vessel 306 is controlled by virtue of the vessel 306 being located in the temperature controlled air chamber 308. In the embodiment shown, the temperature controlled air chamber 308 is held at 60° C., but any suitable temperature may be used. A controller 310 is used to control the temperature in the air chamber 308. A pressure indicator 312 is used to monitor a pressure of the supercritical carbon dioxide. Any suitable pressure indicator may be used. Step 206 of the method 200 comprises delivering the compressed carbon dioxide to a nozzle 314 of the apparatus 300. Alternatively, the compressed carbon dioxide may be delivered directly to the nozzle 314 of the apparatus 300 without any intervening steps, such as temporary storage in a temperature controlled vessel 306.

Step 208 of the method 200 comprises delivering a solution comprising dissolved material for forming nanoparticles from a storage vessel 315 to the nozzle 314 of the apparatus 300. In the embodiment shown, the solution comprises carbamazepine dissolved in methanol. The solution may alternatively comprise any active pharmaceutical ingredient (API), from any of classes I, II, III or IV (according to the biopharmaceutical classification system (BCS)), dissolved in an organic solvent. For example, the API may be or comprise one of carbamazepine, risperidone, ketoprofen, hydrochlorothiazide and fenofibrate. The organic solvent may be or comprise an alcohol, for example methanol. Alternatively, the solution may comprise any suitable solvent in which any suitable material for forming nanoparticles is dissolved, depending on the desired properties of the nanoparticle coating to be formed. In the embodiment shown, the solution is delivered to the nozzle 314 using an Agilent Technologies 1260 Infinity II pump, but any suitable pump may be used. In the embodiment shown, the flow rate of solution delivered to the nozzle 314 is maintained between substantially 0.1 mL·min$^{-1}$ and substantially 0.8 mL·min$^{-1}$, but any suitable flow rate may be used depending, for example, on characteristics of the apparatus 300.

Step 210 of the method 200 comprises mixing supercritical carbon dioxide with the solution comprising dissolved material for forming nanoparticles in the nozzle 314 of the apparatus. In the embodiment shown, the nozzle 314 is a coaxial nozzle having a mixing volume of approximately 0.1 cm$^3$. The solution and the compressed carbon dioxide are delivered to the nozzle 314 separately (for example, via separate fluid lines). In the embodiment shown, the nozzle 314 is maintained at a temperature of substantially 50° C. in order to heat the compressed carbon dioxide delivered to the nozzle 314 to a supercritical state, but any suitable temperature may be used. For example, the temperature may be dependent on the particular solvent used to dissolve the material for forming nanoparticles. In the embodiment shown, the solvent used is methanol which has a boiling point of 65° C. In the embodiment shown, supercritical carbon dioxide pressure is maintained between substantially 9 MPa and substantially 15 MPa, but any suitable pressure of supercritical carbon dioxide may be used. The nozzle 314 is heated using heating resistors (not shown) in close proximity to the nozzle 314, the heating resistors controlled by a controller 314. However, any suitable heating means may alternatively be used. The supercritical carbon dioxide mixes with the solution in the mixing volume of the nozzle 314.

The compressed carbon dioxide may alternatively be heated to supercritical conditions prior to being delivered to the nozzle 314, for example using a heating coil enveloping a pipe containing compressed carbon dioxide. Additionally or alternatively, the solution may be mixed with supercritical carbon dioxide prior to being delivered to the nozzle 314. The method 200 may therefore alternatively comprise delivering a pre-formed mixture of supercritical carbon dioxide and solution to the nozzle 314, rather than separately delivering compressed or supercritical carbon dioxide and solution to the nozzle 314. The nozzle 314 may therefore not be a coaxial nozzle.

Steps 202 to 210 of the method 200 may be replaced by any suitable technique(s) for forming a mixture of supercritical carbon dioxide and solution comprising dissolved material for forming nanoparticles. Exactly how either or both i) the supercritical carbon dioxide, or ii) the mixture of supercritical carbon dioxide and solution are formed is not critical to the invention, as long as the mixture is formed before being introduced into a precipitation chamber 316.

Step 212 of the method 200 comprises spraying the mixture through the nozzle 314 into a precipitation chamber 316 to precipitate nanoparticles. It will be appreciated that means other than the nozzle 314 may be used to introduce the mixture into the chamber 316. The chamber 316 is held at atmospheric pressure. The mixture experiences a rapid pressure drop as the mixture passes through the nozzle 314 into the chamber 316. In the embodiment shown, the nozzle 314 comprises substantially circular nozzle orifices having a diameter of substantially 40 μm. A nozzle 314 having nozzle orifices of any shape, for example square, rectangular, polygonal or other shapes may be used. Any nozzle orifice having a size so as to form nanoparticles on spraying the mixture into the chamber 316 may alternatively be used, for example a nozzle orifice size of substantially 150 μm or smaller, with smaller nozzle orifice sizes (for example 50 μm or smaller) more likely to produce nanoparticles. As the supercritical carbon dioxide depressurizes to form carbon dioxide gas due to the chamber 316 being at atmospheric pressure, nanodroplets (nanosized droplets) of the solution are formed. The supercritical carbon dioxide may therefore act to enhance atomisation of the solution as the mixture passes through the nozzle 314 into the chamber 316. The rapid pressure drop may work in conjunction with the anti-solvent effect of the supercritical carbon dioxide to form the nanodroplets. The chamber 316 being held at atmospheric pressure may also enable the nanodroplets to dry rapidly in order to precipitate nanoparticles. That may enable nanoparticles to be produced and isolated without agglomeration. It will be appreciated that the same could be achieved by using a chamber 316 held at a pressure below a supercritical pressure of the supercritical fluid, enabling the supercritical fluid to depressurize on introduction to the chamber 316. The chamber 316 being held at atmospheric pressure may avoid the need for specialist equipment to pressurize or provide a vacuum in the chamber 316, further reducing cost and complexity.

Additionally or alternatively, process parameters other than nozzle orifice size may be selected or controlled to obtain particles of a desired size. For example, one or more of a flow rate of solution delivered to the nozzle 314, a flow rate of compressed carbon dioxide delivered to the nozzle 314, a density of supercritical carbon dioxide formed in the nozzle 314, a flow rate of drying gas introduced to the chamber 316 (discussed below), and a temperature inside the chamber 316 may influence a size of droplets formed by spraying the mixture through the nozzle 314. A size of the droplets in turn influences a size of particles produced by the method 200. Nanoparticles having a size of substantially 10 nm (or greater) may be produced by controlling one or more of the operating parameters accordingly.

Step 214 of the method 200 comprises introducing a flow of drying gas into the chamber 316. In the embodiment shown, the drying gas comprises a mixture of carbon dioxide gas and nitrogen gas, although it will be appreciated any suitable as or mixture of gases may be used as a drying gas. In the embodiment shown, the drying gas is introduced into the chamber 316 through an inlet 317b from a storage vessel 317a. Using a drying gas in conjunction with a rapid pressure drop may further increase a rate of solvent evaporation from the nanodroplets, leading to faster precipitation of nanoparticles. That may enhance formation and isolation of nanoparticles without agglomeration. Alternatively, a flow of drying gas may not be introduced into the chamber 316, and nanoparticles may be precipitated using only the rapid pressure drop after spray of the mixture from the nozzle 314, and ambient pressure of the chamber 316.

Step 216 of the method 200 comprises capturing precipitated nanoparticles on a bed of fluidized carrier particles located within the chamber 316. The carrier particles are shown schematically in FIG. 3 and are not to scale. In the embodiment shown, the carrier particles comprise microcrystalline cellulose particles, but any suitable excipient or mixture of excipients may alternatively be used. Alternatively, the method 200 may comprise capturing precipitated nanoparticles on one or more items located within the chamber. The one or more items may be or comprise a medical implant, for example a joint replacement implant or a stent. Alternatively, the one or more items may be or comprise other non-medical or non-medicinal items for which a nanoparticle coating is required. Capturing the precipitated nanoparticles on the carrier particles within the chamber 316 may mean that the precipitated nanoparticles are captured on the carrier particles substantially immediately or shortly after precipitation, before having a chance to agglomerate or coalesce. Nanoparticles can be difficult to process or manipulate (for example due to high surface charges), especially after agglomeration. Capturing the nanoparticles shortly after precipitation may avoid the need to manipulate the nanoparticles to overcome such interactions between nanoparticles.

In the embodiment shown, the fluidized bed of carrier particles is supported on a surface within the chamber 316. In the embodiment shown, the surface comprises a partially covered mesh 318. In the embodiment shown, the mesh 318 is formed from steel, but any suitable material may be used. Alternatively, any surface configured to support the fluidized bed of carrier particles and comprising one or more perforations or apertures configured to allow fluid to pass through may be used.

Figure 4A:
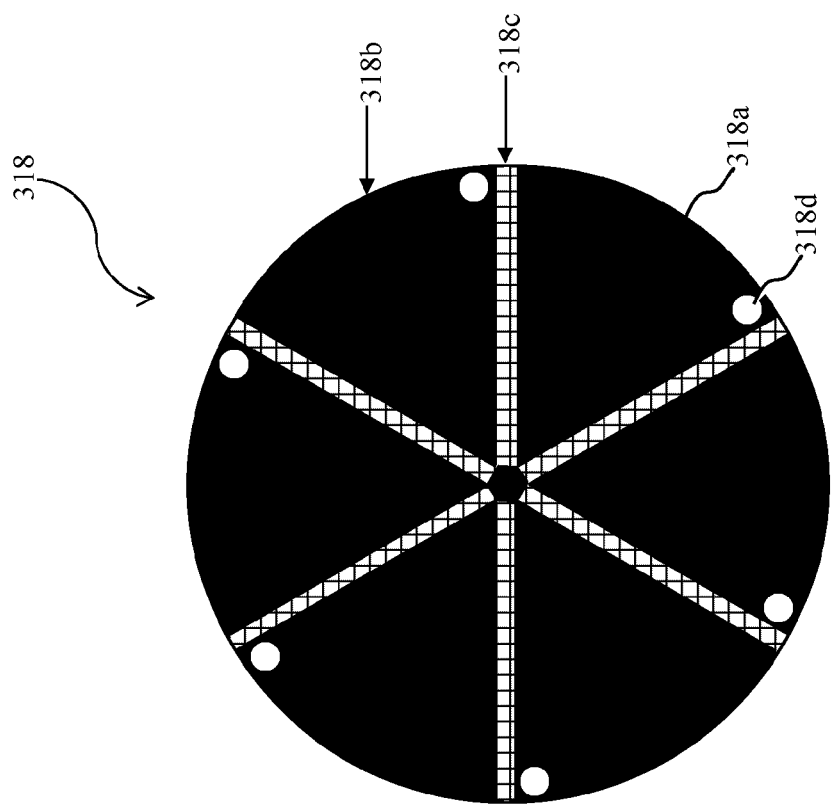
FIG. 4A shows a mesh of the apparatus of FIG. 3 in further detail.

FIG. 4A shows the partially covered mesh 318 in more detail. In the embodiment shown, the mesh 318 comprises a circular shape 318a configured to match an internal cross-sectional shape of the chamber 316. It will be appreciated that a surface or mesh 318 of or comprising any cross-sectional shape could be used to match an internal cross-sectional shape of the chamber 316. A plurality of cover portions 318b are disposed over the mesh 318 to block a plurality of areas of the mesh 318. In the embodiment shown, the cover portions 318b comprise metal plates arranged on either planar face of the mesh 318, although the mesh 318 may alternatively only be covered on one face. The blocked areas of the mesh 318 are therefore unable to allow fluid to pass through. In the embodiment shown, the cover portions 318 each comprise a sector shape, although the cover portions 318 may comprise any suitable shape to block areas of the mesh. Alternatively, the mesh 318 may comprise one cover portion 318b configured to block an area of the mesh 318. In the embodiment shown, the mesh 318 comprises openings of approximately 40 µm in size. In between the cover portions 318b are uncovered areas 318c of the mesh 318. In the embodiment shown, the uncovered areas 318c are approximately 1 cm by 5 cm in dimension. Alternatively, the uncovered areas 318c may have any suitable dimensions. The uncovered areas 318c may have dimensions selected based on one or more of a flow rate of the mixture sprayed through the nozzle 314 and a flow rate of drying gas introduced into the chamber 316. The uncovered areas 318c may enable the chamber 316 to remain at atmospheric pressure, as fluid (for example, residual solvent, depressurised carbon dioxide and drying gas) passing through the mesh 318 escapes the chamber 316 via an outlet 320. The uncovered areas 318c may also have dimensions selected based on a desired process yield. A greater proportion of uncovered areas 318c of the mesh 318 may enable a greater number of precipitated nanoparticles to pass through the mesh 318 without being captured by the carrier particles. The proportion of the mesh 318 comprising uncovered areas 318c may be selected to optimise process yield whilst maintaining atmospheric pressure in the chamber 316. The proportion of the mesh 318 comprising uncovered areas 318c may be dynamically controlled during operation, for example by controlling movement of one or more of the cover portions 318b. In the embodiment shown, each of the cover portions 318b is configured to rotate in either a clockwise or anti-clockwise direction about a pivot point 318d to control a proportion of the mesh 318 comprising uncovered areas 318c. The cover portions 318b may move independently of one another or may all move in the same manner. Alternatively, the cover portions 318b may slide radially inward and outward to expose or cover the mesh 318.

Alternatively, the surface may not comprise cover portions. A shape of the surface may not match the internal cross-sectional shape of the chamber 316, thereby providing paths for fluid to reach the outlet 320 other than by passing through the surface. The surface may therefore not comprise one or more perforations or apertures configured to allow fluid to pass through. Such an arrangement may be suitable if the one or more items comprise a medical implant. A surface having a shape substantially matching an internal cross-sectional shape of the chamber 316 may be preferable for a fluidized bed of carrier particles, to prevent carrier particles from inadvertently being directed to the outlet 320.

In the embodiment shown, a distance between the nozzle 314 and the fluidized bed of carrier particles is substantially 15 cm. That distance may result in an optimal process yield (mass of nanoparticles coating the carrier particles relative to an amount of nanoparticle material introduced to the chamber 316), given other operating parameters such as the uncovered areas 318c of the mesh 318. In the embodiment shown, the process yield is between substantially 50% and substantially 90%. An optimal process yield may also be achieved using a distance between the nozzle 314 and the carrier particles of between substantially 10 cm and substantially 20 cm.

Further increasing the distance may result in a reduced yield, as fewer nanoparticles may be captured by the carrier particles. Conversely, further decreasing the distance may result in wet carrier particles, as solvent from the solution is not able to evaporate completely before the nanodroplets reach the carrier particles.

In the embodiment shown, the flow of carbon dioxide and nitrogen drying gases is used to fluidize the bed of carrier particles. A flow rate of the nitrogen and carbon dioxide gases is adjusted in order to ensure that the bed of carrier particles is fully fluidized. In the embodiment shown, the flow rates of the nitrogen and carbon dioxide gases is substantially 0.4 mL·min$^{-1}$, but any suitable flow rates may be used. In the embodiment shown, the inlet 317b is located adjacent the nozzle 314 on a top of the chamber 316. The flow of drying gas therefore impinges on the bed of carrier particles from above, causing motion of the carrier particles and fluidizing the bed of carrier particles. The impingement of the drying gas on the bed of carrier particles provides elevation to the carrier particles, enabling the carrier particles to efficiently capture the precipitated nanoparticles. The production and isolation of nanoparticles without agglomeration may allow a homogeneous coating of nanoparticles to be formed on the carrier particles.

The flow of drying gas from the inlet 317b and the spray of mixture from the nozzle 314 are oriented in substantially the same direction in the embodiment shown. Alternatively, the inlet 317b may be located on the chamber 316 such that a flow of drying gas introduced into the chamber 316 is not oriented in substantially the same direction as spray of the mixture from the nozzle 314. The flow of drying gas may be, for example, oriented substantially perpendicularly to a direction of spray of the mixture from the nozzle 314. The bed of carrier particles may alternatively be fluidized using alternative means, for example an additional flow of fluidizing gas separate from the drying gas. The mixture may not be sprayed from the nozzle 314 until the bed of carrier particles located within the chamber 316 is fluidized.

Step 218 of the method 200 comprises completing spraying of the mixture from the nozzle 200 and continuing to introduce the flow of drying gas into the chamber 316. In the embodiment shown, a flow of carbon dioxide drying gas is stopped by a flow of nitrogen drying gas is continued to dry residual solvent (for example, residual solvent on the carrier particles). Alternatively, the flow of nitrogen drying gas may be stopped and the flow of carbon dioxide drying gas may be continued to dry residual solvent. The flow of drying gas is continued for substantially 15 minutes after spraying of the mixture from the nozzle 314 is finished, but the flow of drying gas may be continued for any suitable length of time to dry residual solvent (for example, if the carrier particles are wet as a result of a reduced distance between the nozzle 314 and the carrier particles).

Step 220 of the method 200 comprises collecting the nanoparticle coated carrier particles from the chamber 316.

In the embodiment shown, a concentration of the carbamazepine solution may be varied between substantially 20 mg·$L^{-1}$ and substantially 60 mg·$L^{-1}$. Those concentrations are near to but not above a saturation limit of the solution (at the operating parameters set out as described above), and are referred to herein as saturated solutions. It has been found that undersaturated solution results in the production of amorphous nanoparticles using the method 200. In contrast, supersaturated solution (having a concentration above a saturation limit) results in precipitation of crystalline nanoparticles in the nozzle 314 itself, which may lead to blockage of the nozzle 314. Saturated solution results in liquid-like cluster formation (nucleation) of the nanoparticles in the nozzle 314. The clusters convert to crystals upon passing through the nozzle 314 due to formation of nanodroplets which dry rapidly under atmospheric pressure in the chamber 316. In addition, as the mixture of supercritical carbon dioxide and solution is formed in the nozzle 314 in the embodiment shown, there is not sufficient time for nanoparticles to crystallise in the nozzle 314, as residence time of the mixture in the nozzle 314 is of the order of milliseconds. Alternatively, any suitable concentration of solution may be used. For example, if crystalline nanoparticles are not required and amorphous nanoparticles will be satisfactory, an undersaturated solution may be used. A saturated solution may comprise different concentrations for different nanoparticle materials and/or different solvents. A saturated solution may also comprise different concentrations depending on operating parameters such as temperature and pressure (which may determine a saturation limit of the solution).

Varying a concentration of the solution may enable nanoparticle loading onto the carrier particles to be altered or controlled. In the embodiment shown, nanoparticle loading onto the carrier particles is substantially 7.5% for a solution concentration of substantially 20 mg·$L^{-1}$, whereas nanoparticle loading onto the carrier particles is substantially 25% for a solution concentration of substantially 60 mg·$L^{-1}$. A lower concentration of the solution may alternatively be used, which may further reduce nanoparticle loading but may result in an undersaturated solution being used, producing amorphous nanoparticles. As above, a range of concentrations forming a saturated solution may be different for different nanoparticles and/or different solvents. Alternatively, nanoparticle loading onto the carrier particles can be altered or controlled by varying a mass of material for forming nanoparticles introduced into the chamber 316 without changing a concentration of the solution. For example, the solution may be sprayed into the chamber 316 for a greater length of time, which will result in a greater mass of material for forming nanoparticles being introduced to the chamber 316. A greater mass of material for forming nanoparticles introduced into the chamber 316 may result in an increased nanoparticle loading onto the carrier particles, and vice versa. Introducing a greater mass of material for forming nanoparticles into the chamber 316 may increase the possible amount of nanoparticle material that may be captured by the carrier particles (or other items). Controlling loading of nanoparticles onto the carrier particles, particularly in the case of API or anti-bacterial drug nanoparticles, may enable the dose of API or anti-bacterial drug to be accurately controlled.

The method 200 described above relates to a batch process for producing a nanoparticle coating on one or more items, but if required the same method steps may be employed in a continuous process. For example, the spray of mixture from the nozzle 314 (and optionally the spray of drying gas) may be continuous. A continuous bed of carrier particles may be conveyed through the chamber 316 such that uncoated carrier particles are continuously being introduced to the chamber 316 to be coated with nanoparticles.

Figure 4C:
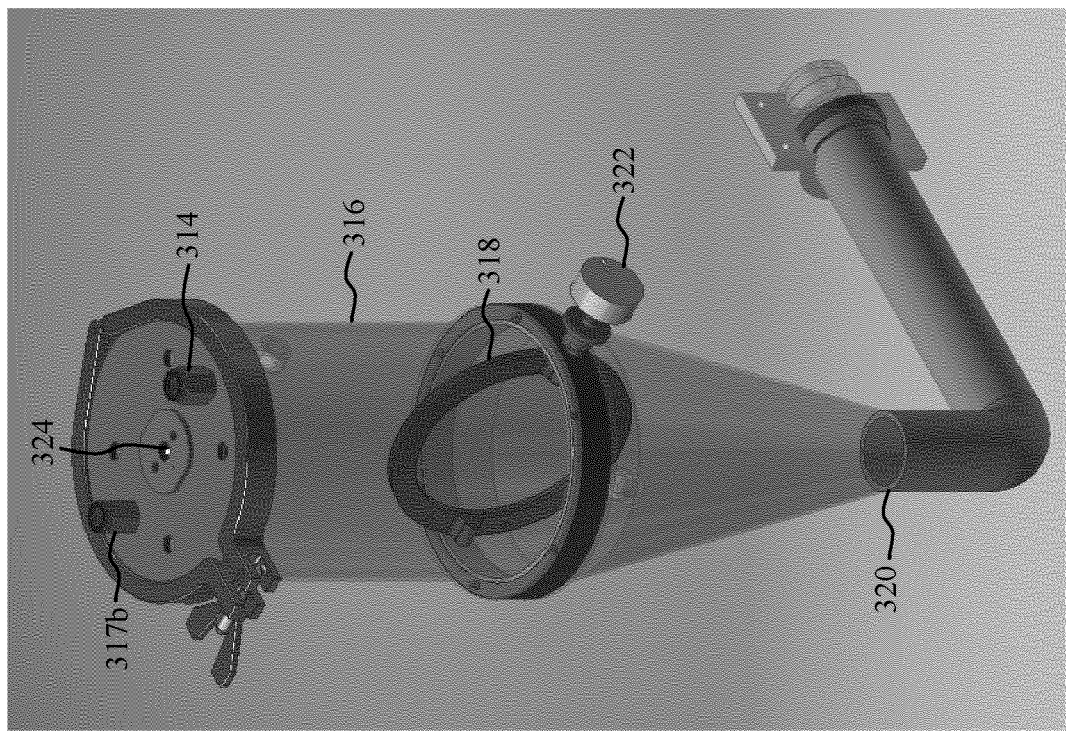
FIGS. 4B and 4C show an alternative rotatable mesh used in the apparatus of FIG. 3.
Figure 4B:
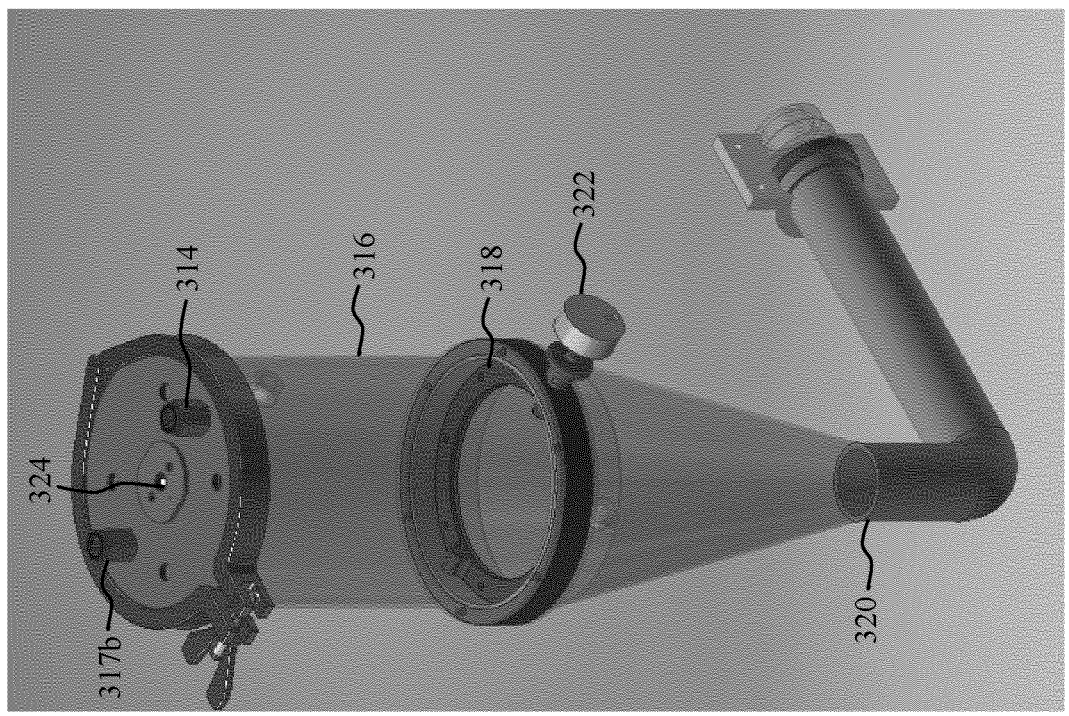

Alternatively, the same method steps may be employed in a semi-continuous process. For example, the surface or mesh 318 on which the one or more items (for example, carrier particles) to be coated are supported may be operable, within the chamber, between a first position or configuration and a second position or configuration, as shown in FIGS. 4B and 4C. FIGS. 4B and 4C show only an outer perimeter of the mesh 318 for clarity. FIG. 4B shows the mesh 318 in a first position configured to support the one or more items for coating. FIG. 4C shows the mesh 318 in a second position configured to allow the coated item(s) to travel or fall towards an outlet 320 of the chamber 316. That may enable a semi-continuous process, by enabling coated items to be removed from the chamber 316 (following the mesh 318 being placed in the second position) and uncoated items to be introduced to the chamber 316 (following the mesh 318 being placed in the first position), without stopping or interrupting spray of the mixture into the chamber 316. The semi-continuous process may therefore effectively comprise substantially continuous spraying of the mixture into the chamber 316 (for example, via the nozzle 314) in conjunction with batch insertion and extraction of items into and out of the chamber 316.

In the embodiment shown, the mesh 318 is arranged substantially parallel to an internal cross-sectional shape of the chamber 316 when the mesh 318 is in the first position. The mesh 318 substantially covers an internal cross-sectional shape of the chamber 316, providing a surface to support the one or more items to be coated and preventing the items from travelling to the outlet 320. In the embodiment shown, the mesh 318 is arranged substantially perpendicular to an internal cross-sectional shape of the chamber 316 when the mesh 318 is in the second position. That minimises a portion of the internal cross-sectional shape of the chamber 316 that the mesh 318 covers, removing the surface on which the items are supported and allowing coated items to travel towards the outlet 320. In the embodiment shown, the mesh 318 is rotatable about an axis between the first position and the second position. The mesh 318 is configured to be rotated via an external handle 322 disposed on the chamber 316, as shown in FIGS. 4B and 4C. The handle 322 may be actuated manually or automatically using a controller. In the embodiment shown, the mesh 318 is freely rotatable through 360° about the axis such that the mesh 318 can be rotated in either direction to move between the first position and the second position. Either face of the mesh 318 may be used to support the one or more items to be coated within the chamber 316.

Alternatively, the mesh 318 may be rotatable through a fixed angle between the first position and the second position, the mesh 318 being rotated in a first direction to move from the first position to the second position and rotated in an opposite direction to return to the first position from the second position. In the embodiment shown, the chamber 316 comprises an inlet 324 through which uncoated items can be introduced into the chamber 316. The inlet 324 may be in fluid communication with a feed hopper (not shown) containing uncoated items. The inlet 324 may be sealable (for example, manually or automatically using a controller) to selectively introduce uncoated items into the chamber 316 when the mesh 318 is in the first position.

The method 200 described above relates to production of a nanoparticle coating on one or more items. However, the methods 100, 200 described above are not limited to producing nanoparticles or nanoparticle coatings. Different particle sizes may be produced using the methods 100, 200, for example by altering a nozzle orifice size of the nozzle 314 through which the mixture is sprayed into the chamber 316. A larger nozzle orifice size may produce larger droplets of solution as the mixture enters the precipitation chamber 316. Conversely, smaller nozzle orifices may produce smaller droplets of solution as the mixture enters the precipitation chamber 316. The rapid pressure drop as the mixture is sprayed into the chamber 316 through the nozzle 314 may result in rapid evaporation of the solvent in the droplets, irrespective of the droplet size. The rate of solvent evaporation may be further increased by a flow of drying gas. The particle size produced may therefore be substantially dictated by a size of solution droplets formed by spraying the mixture through the nozzle 314.

In the embodiment of the method 200 described above, the carrier particles to be coated are supported on the mesh 318. For coating larger items such as medical implants including joint replacement implants or stents, the items may be supported on a surface such as the mesh 318. Alternatively, the larger items may be supported by or affixed to a sidewall of the chamber 316 to enable efficient coating of particles on the larger items. For example, the larger items may be supported on a platform or shelf extending from a sidewall of the chamber 316, or may be affixed directly to a sidewall of the chamber 316 (for example, using adhesive or a clamp mechanism).

Tables 1 and 2 and FIGS. 5 to 8 show experimental results obtained for several examples using the method 200 described above. In the examples shown, API nanoparticles of carbamazepine (CBZ), risperidone (RIS) and ketoprofen (KET) respectively were coated onto excipient carrier particles formed from microcrystalline cellulose (MCC).

TABLE 1

Results of API nanoparticle size, polymorphism and process yield obtained using the method 200 to coat excipient carrier particles of microcrystalline cellulose with API nanoparticles of one of carbamazepine, risperidone or ketoprofen at 10% loading.

| API | Run No. | Size/nm | Polymorphism | Yield/% |
|---|---|---|---|---|
| Carbamazepine | 1 | 180 ± 52 | FIII | 75 ± 0.7 |
| | 2 | 196 ± 89 | FIII | 61 ± 1.3 |
| | 3 | 126 ± 43 | FIII | 73 ± 0.7 |
| Risperidone | 1 | 360 ± 90 | Form B | 76 ± 2.9 |
| | 2 | 316 ± 68 | Form B | 67 ± 6.0 |
| | 3 | 345 ± 93 | Form B | 62 ± 10 |
| Ketoprofen | 1 | 490 ± 160 | FI | 58 ± 3.7 |
| | 2 | 380 ± 70 | FI | 62 ± 1.7 |
| | 3 | 380 ± 75 | FI | 89 ± 2.6 |

TABLE 2

Results of API nanoparticle size, polymorphism and process yield obtained using the method 200 to coat excipient carrier particles of microcrystalline cellulose with API nanoparticles of one of carbamazepine, risperidone or ketoprofen at 20% loading.

| API | Run No. | Size/nm | Polymorphism | Yield/% |
|---|---|---|---|---|
| Carbamazepine | 1 | 111 ± 56 | FIII | 73 ± 2.2 |
| | 2 | 126 ± 59 | FIII | 71 ± 2.0 |
| | 3 | 90 ± 28 | FIII | 62 ± 1.3 |
| Risperidone | 1 | 340 ± 75 | Form B | 76 ± 1.8 |
| | 2 | 307 ± 77 | Form B | 72 ± 6.0 |
| | 3 | 286 ± 69 | Form B | 70 ± 6.0 |
| Ketoprofen | 1 | 460 ± 280 | FI | 49 ± 3.2 |
| | 2 | 310 ± 80 | FI | 79 ± 9.2 |
| | 3 | 325 ± 85 | FI | 77 ± 0.8 |

The results shown in Tables 1 and 2 were obtained using an API concentration of substantially 50 mg·mL$^{-1}$, a supercritical carbon dioxide pressure of substantially 10 MPa, and an API flow rate of substantially 0.4 mL·min$^{-1}$. The API concentration used results in the formation of a saturated solution as discussed above. In respect of CBZ, an additive concentration of 10 wt. % was also included in the solution. The additive used was sodium dodecyl sulfate and was included to promote formation of the stable carbamazepine polymorph Form III (discussed below). It will be appreciated that it is not essential the solution includes such additives, or that one or more different additives could be used. As can be seen from the results set out in Tables 1 and 2, the API nanoparticle size produced in the examples shown is between substantially 90 nm and substantially 500 nm in all cases. The process yield in the examples shown is between substantially 50% and substantially 90% in all cases, where the yield is defined as shown in Equation 1:

$$\text{Yield} = \frac{\text{mass of } API \text{ material coated onto excipient}}{\text{mass of } API \text{ material sprayed}} \times 100 \quad \text{Equation 1}$$

The results shown in Table 1 were obtained at API loading of 10 wt. %, whilst the results shown in Table 2 were obtained at API loading of 20 wt. %. The loading is defined as shown in Equation 2:

$$\text{Loading} = \frac{\text{mass of } API \text{ material sprayed}}{\text{mass of } API \text{ material sprayed} + \text{mass of excipient}} \times 100 \quad \text{Equation 2}$$

Figure 3:
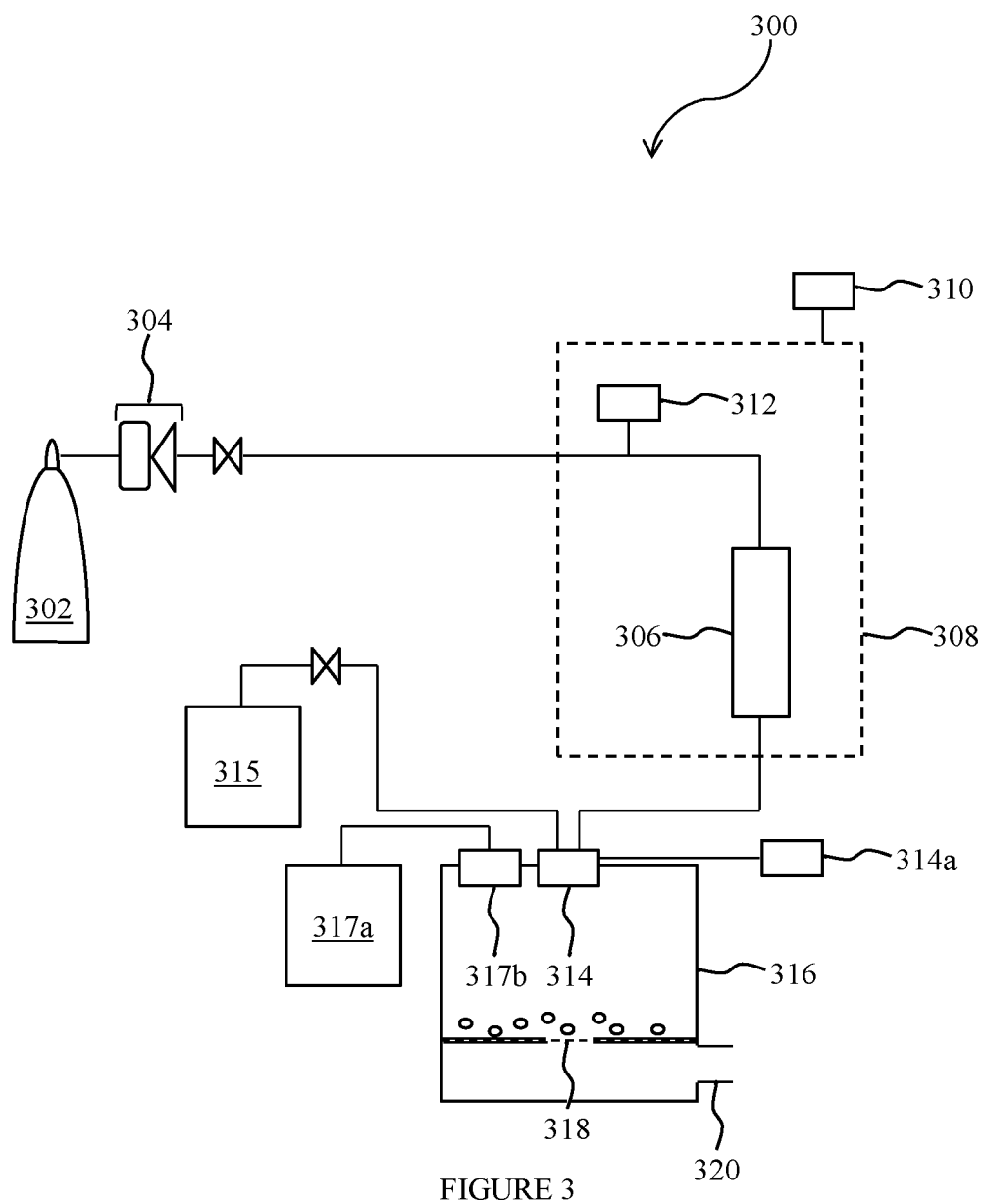
FIG. 3 shows an embodiment of an apparatus for use in the method of FIG. 2 in accordance with the invention.
Figures 5A, 5B, 5C:
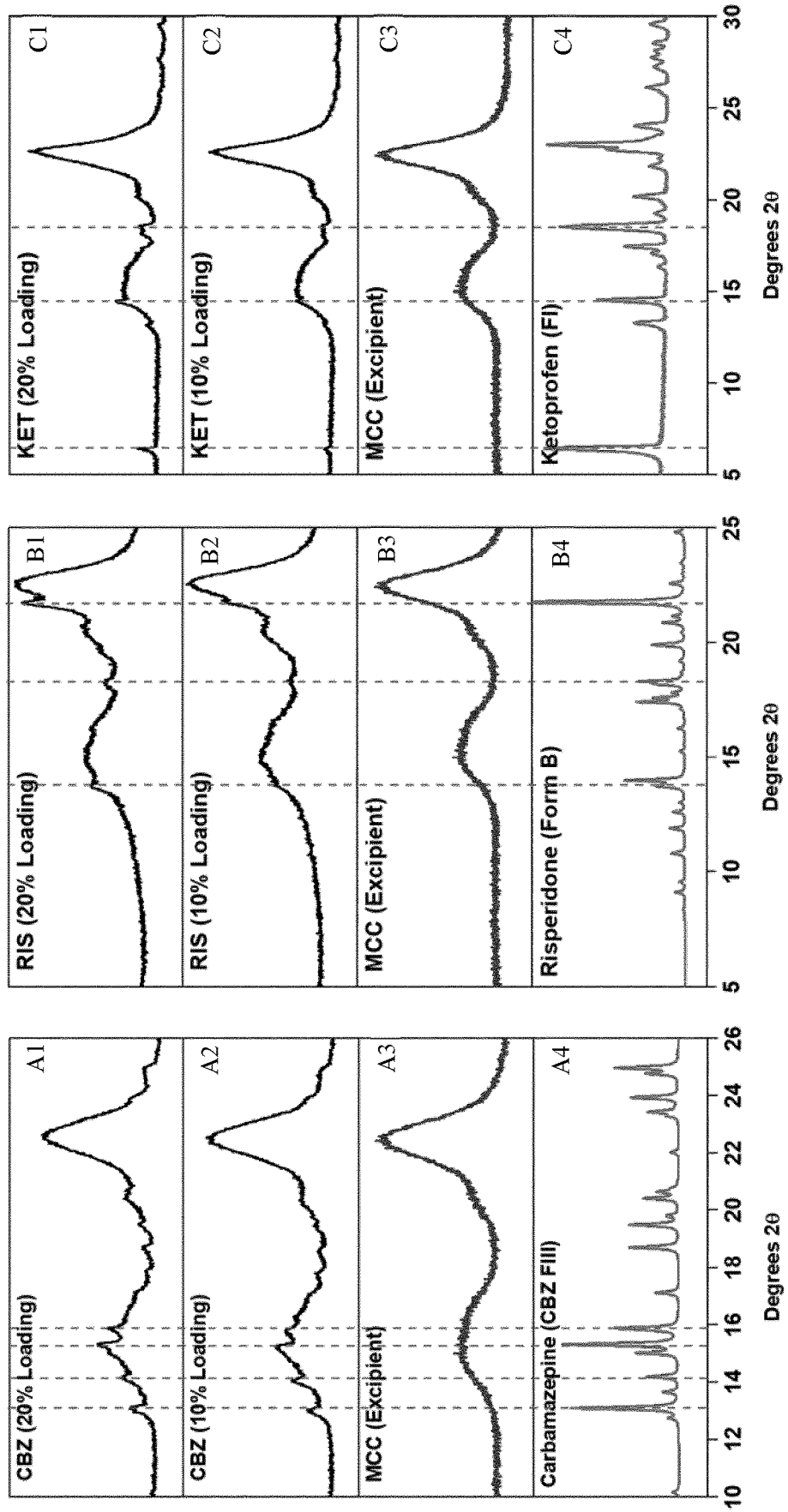
FIGS. 5A to 5C show X-ray diffraction (XRD) patterns for nanoparticle coated carrier particles produced by the method shown in FIG. 2.

FIGS. 5A to 5C show X-ray diffraction (XRD) patterns obtained for the coated carrier particles of Tables 1 and 2. FIG. 5A is discussed in further detail below. FIG. 5A1 shows an XRD pattern obtained for MCC carrier particles coated with CBZe nanoparticles at 20 wt. % loading. FIG. 5A2 shows an XRD pattern obtained for MCC carrier particles coated with CBZ nanoparticles at 10 wt. % loading. FIG. 5A3 shows an XRD pattern for MCC without CBZ nanoparticles. FIG. 5A4 shows an XRD pattern for the CBZ polymorph FIII.

A location of some dominant peaks on the XRD pattern of FIG. 5A4 is mapped onto the XRD patterns of FIGS. 5A1 and 5A2 respectively, using the dashed lines running across each of FIGS. 5A1 to 5A4. It can be seen that locations of the peaks in the XRD pattern of FIG. 5A4 directly correspond to locations of peaks in the XRD patterns of FIGS. 5A1 and 5A2 respectively. By visual comparison of FIGS. 5A1, 5A2, 5A3 and 5A4, it is evident that the XRD patterns of FIGS. 5A1 and 5A2 show the XRD pattern for MCC superimposed with the XRD pattern for the CBZ FIII polymorph. That indicates that the polymorphic form of CBZ nanoparticles coated onto the MCC carrier particles is the stable FIII form, confirming that the method 200 may produce crystalline nanoparticles at suitable concentrations (concentrations forming a saturated solution as discussed above). The peak intensities for the CBZ polymorph FIII are slightly higher in FIG. A1 than FIG. A2. The increased peak intensities likely reflect the greater mass of CBZ nanoparticles coating the MCC carrier particles at higher loading, leading to a more intense signal.

FIGS. 5B and 5C show similar XRD patterns to those shown in FIG. 5A, but for carrier particles coated with RIS and KET respectively. FIG. 5B shows that the polymorphic form of RIS nanoparticles produced is the metastable Form B, whilst FIG. 5C shows that the polymorphic form of KET nanoparticles produced is the stable FI form. FIGS. 5B and 5C add further confirmation that the method 200 may result in the formation of crystalline nanoparticles.

Figure 6A:
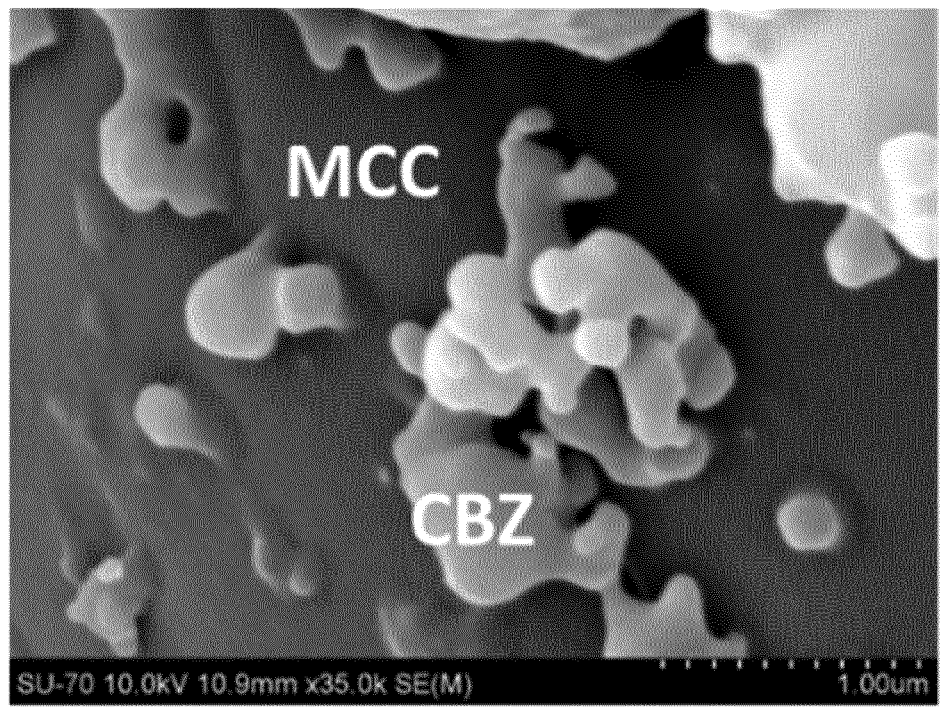
FIGS. 6A to 6C show scanning electron microscope (SEM) micrographs of the nanoparticle coated carrier particles produced by the method shown in FIG. 2.
Figure 6A:
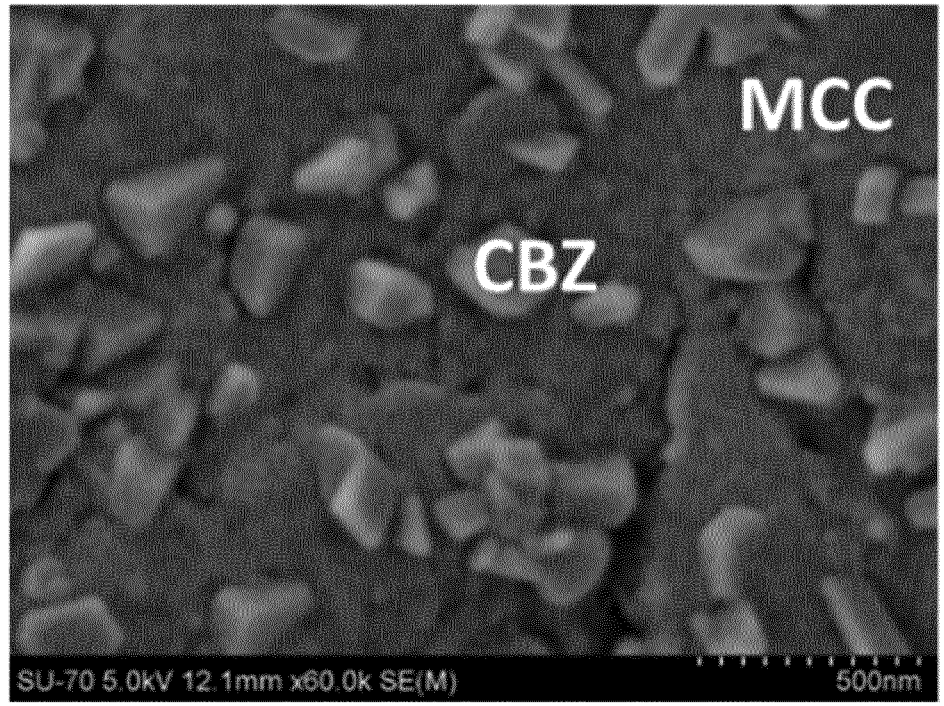
Figure 6B:
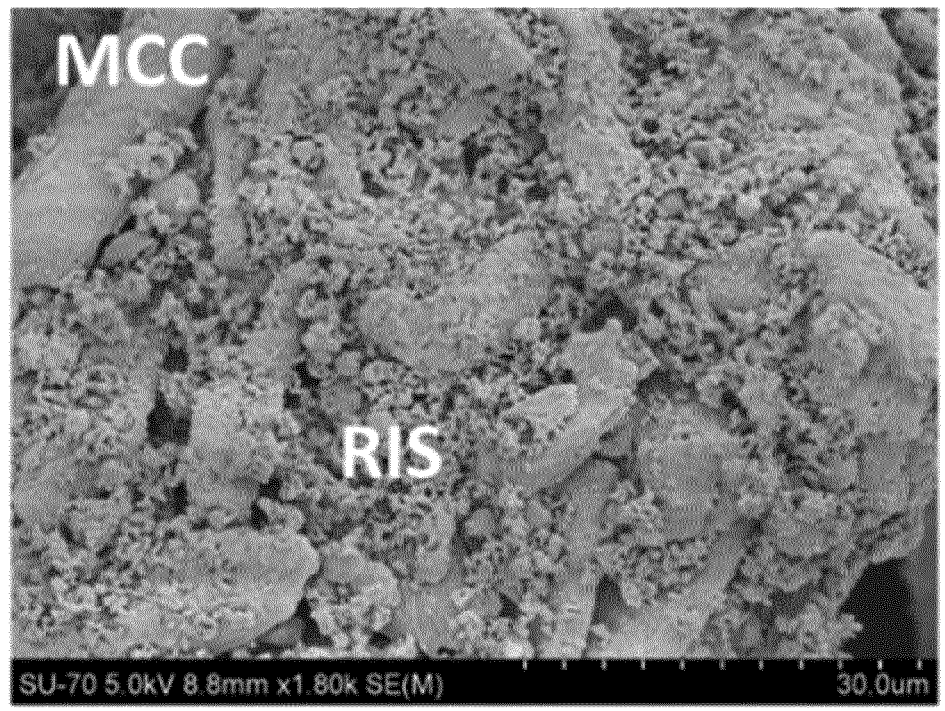
Figure 6B:
Figure 6C:
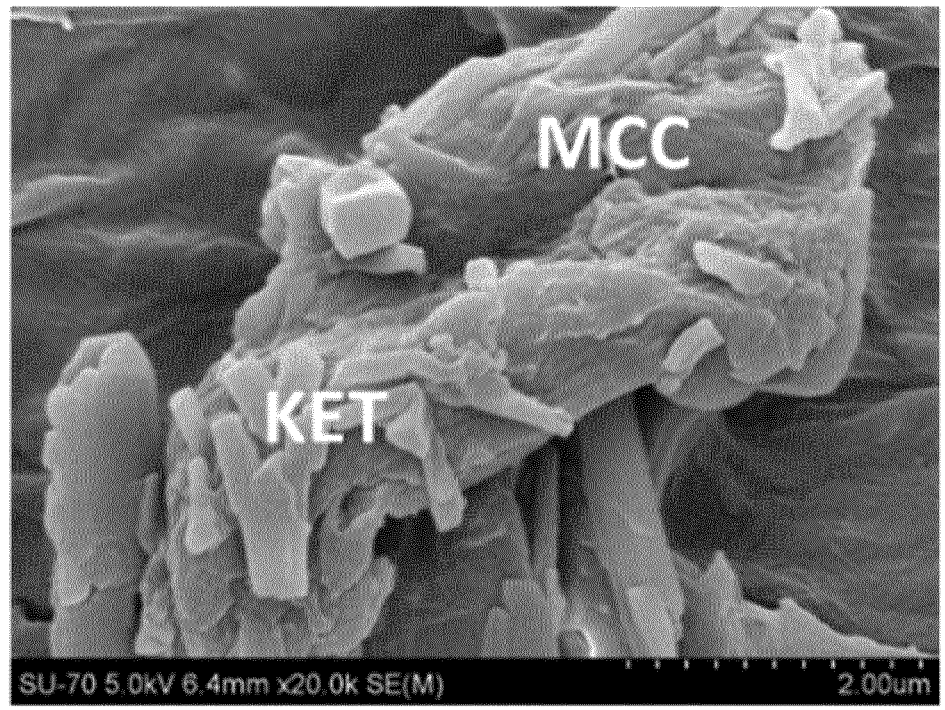
Figure 6C:
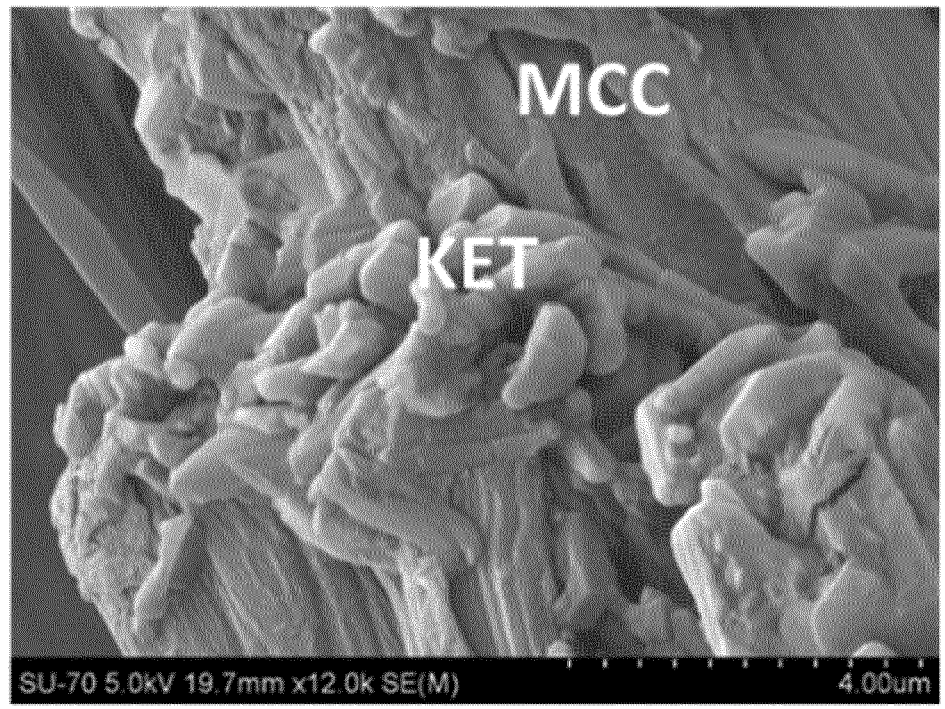

FIGS. 6A to 6C show scanning electron microscope (SEM) micrographs of the coated carrier particles of Tables 1 and 2.

FIG. 6A1 shows a SEM micrograph of MCC carrier particles coated with CBZ nanoparticles at 10 wt. % loading. The micrograph has a magnification of ×35000, and a scale bar showing 1.00 μm is included at the bottom right hand corner FIG. 6A1. An accelerating voltage of 10.0 kV was used at a working distance of 10.9 mm.

FIG. 6A2 shows a SEM micrograph of MCC carrier particles coated with CBZ nanoparticles at 20 wt. % loading. The micrograph has a magnification of ×60000, and a scale bar showing 500 nm is included at the bottom right hand corner of FIG. 6A2. An accelerating voltage of 5.0 kV was used at a working distance of 12.1 mm.

In both FIGS. 6A1 and 6A2, the darker, continuous regions of the micrographs indicate MCC, whilst the lighter, discontinuous (i.e., particulate) regions indicate CBZ nanoparticles, as shown by the annotations MCC and CBZ respectively. The distribution of the lighter regions in FIGS. 6A1 and 6A2 illustrates that the method 200 results in a homogeneous coating of CBZ nanoparticles on the MCC carrier particles. FIG. 6A1 shows that the CBZ nanoparticles are coated onto the MCC carrier particles substantially individually. The CBZ nanoparticles can be distinguished and seen distinctly from one another. The increased loading of 20 wt. % is illustrated in FIG. 6A2 by the reduced spacing between adjacent CBZ nanoparticles coated onto the MCC carrier particles. However, similar to FIG. 6A1 the CBZ nanoparticles are also coated onto the MCC carrier particles substantially individually, maintaining a homogeneous coating of CBZ nanoparticles.

FIG. 6B1 shows a SEM micrograph of MCC carrier particles coated with RIS nanoparticles at 10 wt. % loading. The micrograph has a magnification of ×1800, and a scale bar showing 30.0 μm is included at the bottom right hand corner of FIG. 6B1. An accelerating voltage of 5.0 kV was used at a working distance of 8.8 mm.

FIG. 6B2 shows a SEM micrograph of MCC carrier particles coated with RIS nanoparticles at 20 wt. % loading. The micrograph has a magnification of ×18000, and a scale bar showing 3.00 μm is included at the bottom right hand corner of FIG. 6B2. An accelerating voltage of 5.0 kV was used at a working distance of 8.8 mm.

In FIG. 6B1, the more discontinuous (granular or speckled) regions of the micrograph indicate the presence of RIS nanoparticles, whilst the more continuous regions indicate MCC, as shown by the annotations RIS and MCC respectively. FIG. 6B1 clearly illustrates a homogeneous distribution of RIS nanoparticles on the surface of the MCC carrier particles. No significant agglomeration of the RIS nanoparticles can be seen in FIG. 6B1. FIG. 6B2 has a higher magnification than FIG. 6B1 at a higher loading of 20 wt. %. FIG. 6B2 shows a homogeneous coating of individual RIS nanoparticles coated onto the MCC carrier particles. The RIS nanoparticles can be distinguished and seen distinctly from one another. The higher loading results in a surface of the MCC carrier particles being substantially covered with RIS nanoparticles. No MCC carrier particle surface can be seen in the micrograph of FIG. 6B2.

FIG. 6C1 shows a SEM micrograph of MCC carrier particles coated with KET nanoparticles at 10 wt. % loading. The micrograph has a magnification of ×20000, and a scale bar showing 2.00 μm is included at the bottom right hand corner of FIG. 6C1. An accelerating voltage of 5.0 kV was used at a working distance of 6.4 mm.

FIG. 6C2 shows a SEM micrograph of MCC carrier particles coated with KET nanoparticles at 20 wt. % loading. The micrograph has a magnification of ×12000, and a scale bar showing 4.00 μm is included at the bottom right hand corner of FIG. 6C2. An accelerating voltage of 5.0 kV was used at a working distance of 19.7 mm.

In FIGS. 6C1 and 6C2, the discontinuous, lighter regions of the micrograph indicate KET nanoparticles, whilst the more continuous, darker regions indicate MCC carrier particles, as shown by the annotations KET and MCC respectively. Both FIGS. 6C1 and 6C2 clearly illustrate that the KET nanoparticles are captured on the MCC carrier particles substantially individually. The individual nanoparticles can be distinguished and seen distinctly from one another. FIGS. 6C1 and 6C2 therefore show a homogeneous coating of KET nanoparticles on the MCC carrier particles. The higher loading of 20 wt. % in FIG. 6C2 is reflected by an increased surface of the MCC carrier particles being coated in KET nanoparticles.

FIGS. 6A to 6C clearly demonstrate that the method 200 results in a homogeneous coating of API nanoparticles on the MCC carrier particles. The precipitated API nanoparticles may be captured on the surface of the MCC carrier particles individually before agglomerating. The average size and standard deviation of the API nanoparticles was also determined from the SEM micrographs, using a minimum of 150 nanoparticles for each sample.

Figure 7A:
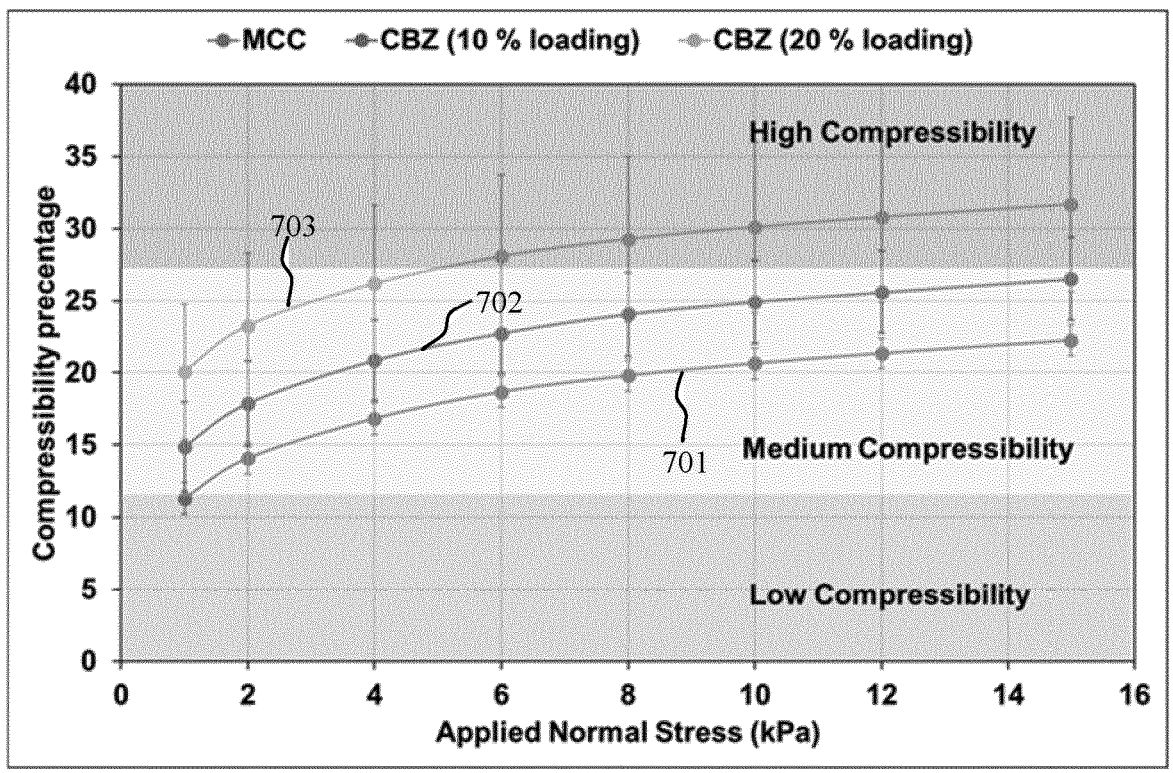
FIGS. 7A to 7C show plots of compressibility percentage as a function of applied normal stress for the nanoparticle coated carrier particles produced by the method shown in FIG. 2.
Figure 7B:
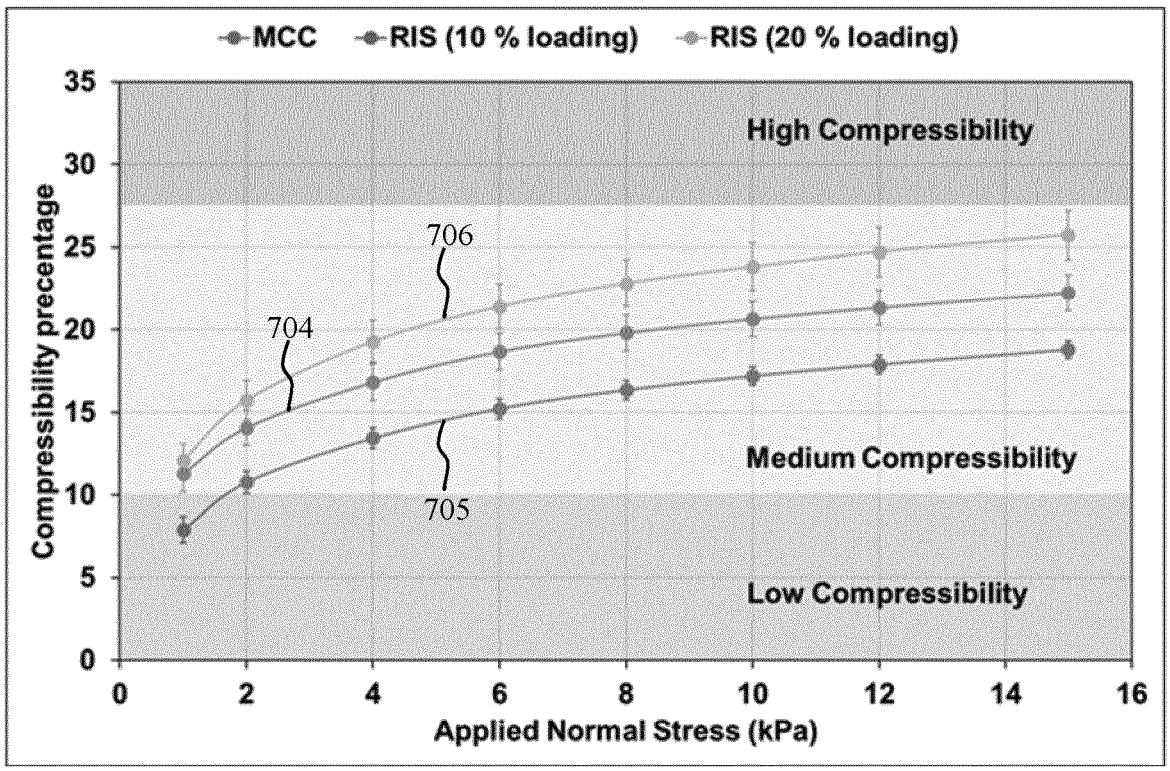
Figure 7C:
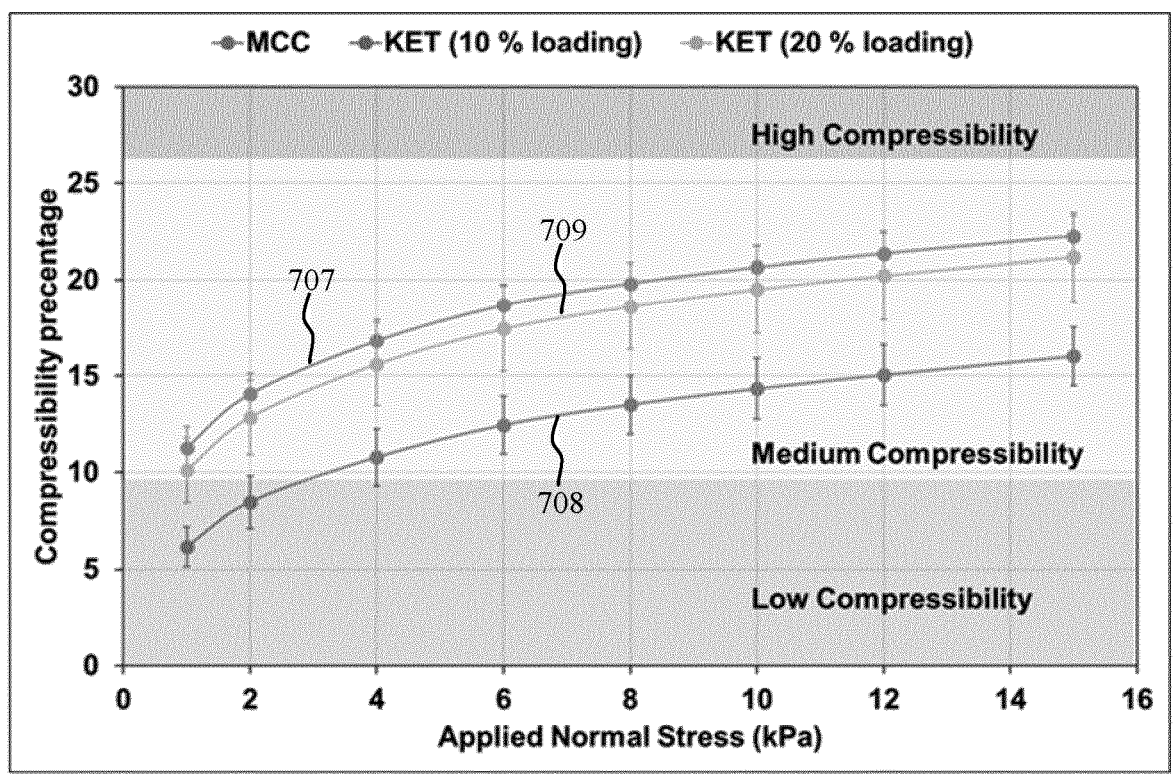

FIGS. 7A to 7C show plots of compressibility percentage as a function of applied normal stress for the coated carrier particles of Tables 1 and 2.

FIG. 7A shows three plots 701, 702, 703 of compressibility percentage as a function of applied normal stress in kPa. Plot 701 shows data for uncoated MCC carrier particles. Plot 702 shows data for MCC carrier particles coated with CBZ nanoparticles at a loading of 10 wt. %. Plot 703 shows data for MCC carrier particles coated with CBZ nanoparticles at a loading of 20 wt. %.

All three plots 701, 702, 703 exhibit a similar shape. The rate of increase of compressibility percentage as a function of applied normal stress decreases as the magnitude of applied normal stress increases. FIG. 7A shows that the compressibility percentage for plot 702 is approximately 5 percentage points higher than the compressibility percentage for plot 701 all applied normal stresses. In turn, the compressibility percentage for plot 703 is approximately 5 percentage points higher than the compressibility percentage for plot 702 at all applied normal stresses. That indicates that increased CBZ nanoparticle loading actually increases compressibility percentage of MCC carrier particles. In particular, at a low applied normal stress of substantially 1 kPa, the compressibility percentage of plot 701 is in the low compressibility regime. Conversely, the compressibility percentage of plots 702 and 703 is in the medium compressibility regime at a low applied stress of substantially 1 kPa. At low applied normal stresses, providing a homogeneous CBZ nanoparticle improves the rheological properties (such as compressibility) of CBZ nanoparticles, thereby improving processability of CBZ into a final form.

FIG. 7B shows three plots 704, 705, 706 of compressibility percentage as a function of applied normal stress in kPa. Plot 704 shows data for uncoated MCC carrier particles. Plot 705 shows data for MCC carrier particles coated with RIS nanoparticles at a loading of 10 wt. %. Plot 706 shows data for MCC carrier particles coated with RIS nanoparticles at a loading of 20 wt. %.

Similar to FIG. 7A, all three plots 704, 705, 706 exhibit a similar shape, in that the rate of increase in compressibility percentage decreases as the magnitude of applied normal stress increases. Plot 705 is approximately 3 or 4 percentage points lower than plot 704 at all applied normal stresses, but remains substantially in the medium compressibility regime for the majority of applied normal stresses between 1 kPa and 15 kPa. Plot 706 is between approximately 1 and 5 percentage points higher than plot 704 at all applied normal stresses, with the difference increasing as the magnitude of applied normal stress increases. For the example of MCC carrier particles coated with RIS nanoparticles, nanoparticle coating at 10 wt. % loading slightly decreases compressibility percentage of MCC carrier particles, whilst nanoparticle coating at 20 wt. % loading slightly increases the compressibility percentage of MCC carrier particles.

However, for both 10 wt. % loading and 20 wt. % loading, the compressibility behaviour of the MCC carrier particles is similar to the compressibility of uncoated MCC carrier particles. FIG. 7B clearly illustrates that providing MCC carrier particles with a homogeneous RIS nanoparticle coating substantially retains the rheological properties (such as compressibility) of uncoated MCC carrier particles. That may improve processability of RIS into a final form compared to handling RIS nanoparticles which are not coated onto carrier particles. For example, due to nanoparticle agglomeration, the rheological properties of RIS nanoparticles not coated onto carrier particles may be significantly worse than the rheological properties of carrier particles coated with RIS nanoparticles.

FIG. 7C shows three plots 707, 708, 709 of compressibility percentage as a function of applied normal stress in kPa. Plot 707 shows data for uncoated MCC carrier particles. Plot 708 shows data for MCC carrier particles coated with KET nanoparticles at a loading of 10 wt. %. Plot 709 shows data for MCC carrier particles coated with KET nanoparticles at a loading of 20 wt. %.

Similar to FIGS. 7A and 7B, all three plots 707, 708, 709 exhibit a similar shape, in that the rate of increase in compressibility percentage decreases as the magnitude of applied normal stress increases. Plot 709 is approximately 1 percentage point lower than plot 707 at all applied normal stresses. Plot 708 is approximately 5 percentage points lower than plot 707 at all applied normal stresses, but remains substantially in the medium compressibility regime for the majority of applied normal stresses between 1 kPa and 15 kPa FIG. 7C demonstrates that providing MCC carrier particles with a homogeneous KET nanoparticle coating substantially retains the rheological properties (such as compressibility) of uncoated MCC carrier particles. That may improve processability of KET into a final form compared to handling KET nanoparticles which are not coated onto carrier particles. For example, due to nanoparticle agglomeration, the rheological properties of KET nanoparticles not coated onto carrier particles may be significantly worse than the rheological properties of carrier particles coated with KET nanoparticles.

FIGS. 7A to 7C clearly demonstrate that the rheological properties of larger carrier particles are substantially retained or even enhanced when producing a homogeneous coating of API nanoparticles on the carrier particles. Processability of the API material into a final oral dosage form (for example, tablet form) may therefore be improved by producing a homogeneous coating of API nanoparticles on excipient carrier particles.

The Hausner's ratio and the compressibility index (compressibility percentage) were calculated at an applied stress of 4 kPa for each of the plots 701 to 709 described above, to evaluate the flow properties of the nanoparticle coated carrier particles. The Hausner's ratio and compressibility index are determined by measuring both the bulk volume and the tapped or compressed volume of a powder, calculated as shown in Equation 3 and Equation 4 respectively below. In the embodiment shown, a Freeman Technology FT4 Rheometer was used to perform the compressibility measurement by applying an increasing level of compression force with a vented piston to a conditioned powder and measuring the change in volume as a function of applied load. The vented piston ensures that air trapped within the powder is able to readily escape, allowing for precise definition of compressibility expressed as a percentage change in volume for a given applied normal stress.

$$\text{Compressibility Index} = 1 - \left(\frac{V_0 - V_f}{V_0}\right) \quad \text{Equation 4}$$

$$\text{Hausner ratio} = \frac{V_0}{V_f}$$

$V_0$ represents the bulk volume of the sample, whilst $V_f$ represents the compressed or tapped volume of the sample. Powders presenting a compressibility index of up to 25 are considered to have acceptable flow properties. The Hausner's ratio is related to inter-particle friction and powders with low inter-particle friction presenting a Hausner's ratio of up to 1.35 are considered to have acceptable flow properties. As illustrated in Table 3 below, all of the samples including uncoated MCC carrier particles, nanoparticle coated MCC carrier particles at 10 wt. % loading and nanoparticle coated MCC carrier particles at 20 wt. % loading exhibited acceptable flow properties, with the exception of CBZ nanoparticle coated MCC carrier particles at 20 wt. % loading. That could be due to a large number of free CBZ nanoparticles in the CBZ-MCC composite, leading to an increase in compressibility index and Hausner's ratio.

TABLE 3

Results of compressibility index (in %) and Hausner's ratio for nanoparticle coated MCC carrier particles at 10 wt. % loading and 20 wt. % loading, together with uncoated MCC carrier particles, at an applied stress of 4 kPa.

| Loading | Sample | Powder compressibility | |
|---|---|---|---|
| | | Average compressibility index (%) ± SD | Average Hausner's ratio ± SD |
| Uncoated | MCC | 16.8 ± 1.1 | 1.2 ± 0.02 |
| 10 wt. % | CBZ | 20.9 ± 2.8 | 1.3 ± 0.04 |
| | RIS | 13.5 ± 0.6 | 1.2 ± 0.01 |
| | KET | 10.8 ± 1.5 | 1.1 ± 0.02 |
| 20 wt. % | CBZ | 26.2 ± 2.9 | 1.4 ± 0.05 |
| | RIS | 19.3 ± 1.3 | 1.2 ± 0.02 |
| | KET | 15.6 ± 2.2 | 1.2 ± 0.03 |

SD: standard deviation.

Figure 8A:
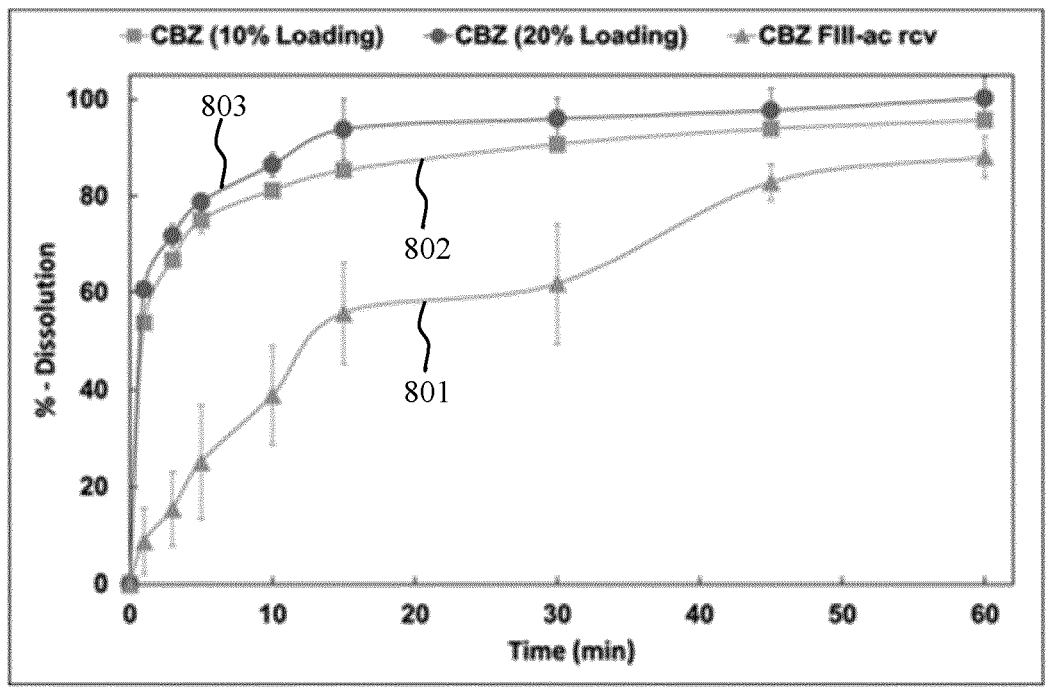
FIGS. 8A to 8C show plots of dissolution percentage as a function of time for the nanoparticle coated carrier particles produced by the method shown in FIG. 2.
Figure 8B:
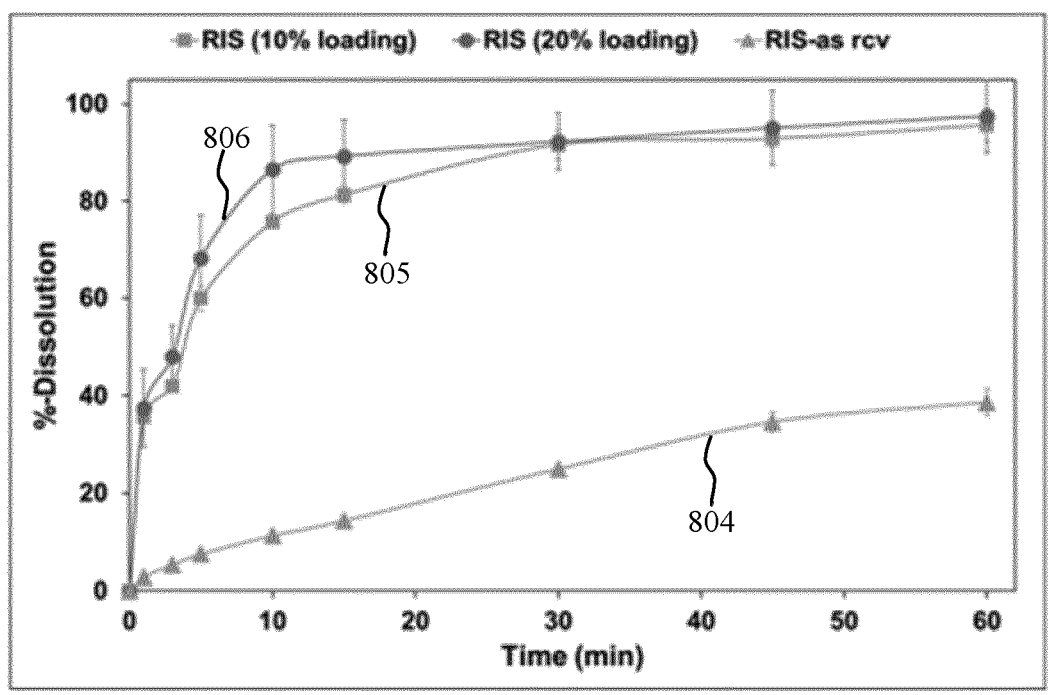
Figure 8C:
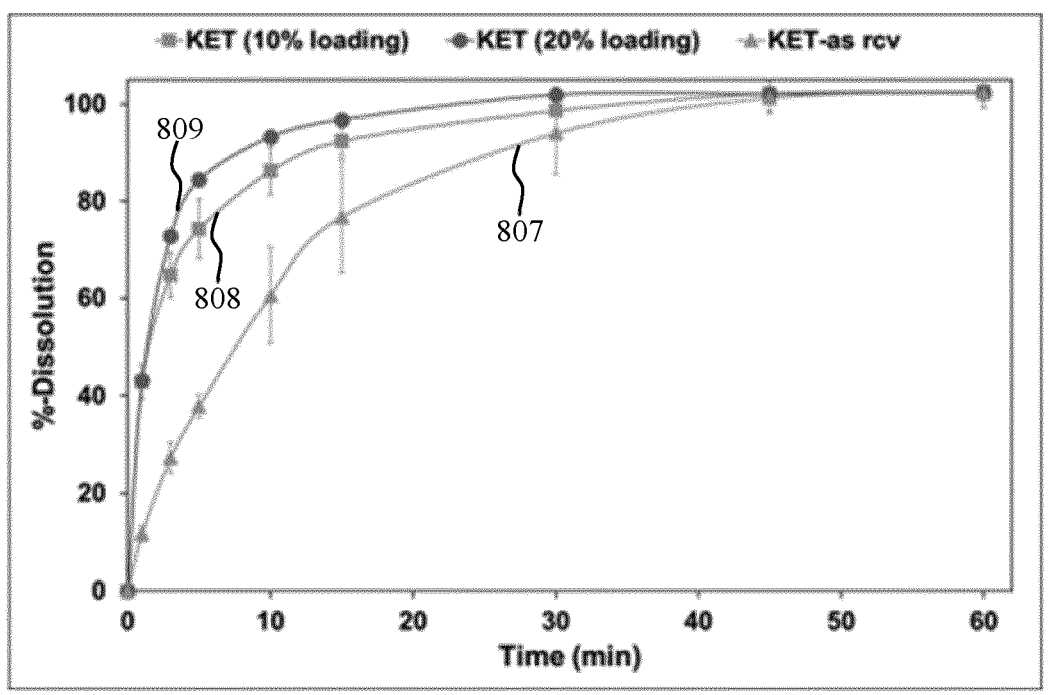

FIGS. 8A to 8C show plots of dissolution percentage as a function of time for the coated carrier particles of Tables 1 and 2.

FIG. 8A shows three plots 801, 802, 803 of CBZ dissolution percentage as a function of time. Plot 801 shows data for CBZ as received as the stable polymorph Form III. Plot 802 shows data for MCC carrier particles coated with CBZ nanoparticles at a loading of 10 wt. %. Plot 803 shows data for MCC carrier particles coated with CBZ nanoparticles at a loading of 20 wt. %.

The dissolution percentage as a function of time was measured by respectively dissolving the as received CBZ and the coated MCC carrier particles in methanol (although other dissolution media could be used). UV spectrophotometry was used to measure the concentration of the CBZ dissolved in the methanol.

Plots 802 and 803 show a much higher dissolution rate of CBZ when loaded onto MCC carrier particles as a homogeneous coating of nanoparticles than in its as received form. It can clearly be seen in FIG. 8A that both plots 802 and 803 exhibit a very steep gradient at the left hand-side of FIG. 8A, indicating a very high initial dissolution rate of CBZ. Plot 802 shows that substantially 80% of the CBZ loaded onto the MCC carrier particles is dissolved within 10 minutes whilst plot 803 shows that substantially 85% of CBZ is dissolved within 10 minutes. The gradient of plots 802 and 803 then becomes much flatter as time increases, illustrating that the dissolution rate decreases significantly once the majority of the CBZ has been dissolved. In contrast, plot 801 shows a much shallower gradient at the left hand side of FIG. 8A, indicating a much lower initial dissolution rate of CBZ. Plot 801 shows that less than 40% of the as received CBZ is dissolved within 10 minutes. Plot 801 becomes shallower and steeper in places, but generally maintains a steady dissolution rate reaching approximately 80% CBZ dissolution after approximately 50 minutes.

FIG. 8B shows three plots 804, 805, 806 of RIS dissolution percentage as a function of time. Plot 804 shows data for RIS as received. Plot 805 shows data for MCC carrier particles coated with RIS nanoparticles at a loading of 10 wt. %. Plot 806 shows data for MCC carrier particles coated with RIS nanoparticles at a loading of 20 wt. %.

Similar to plots 802, 803 in FIG. 8A, plots 805 and 806 show a much higher dissolution rate of RIS when loaded onto MCC carrier particles as a homogeneous coating of nanoparticle than its as received form. It can clearly be seen in FIG. 8B that both plots 805 and 806 exhibit a very steep gradient at the left-hand side of FIG. 8B, indicating a very high initial dissolution rate of RIS. Plot 805 shows that substantially 75% of RIS loaded onto the MCC carrier particles is dissolved within 10 minutes whilst plot 806 shows that substantially 85% of RIS is dissolved within 10 minutes. The gradient of plots 805 and 806 then becomes much flatter as time increases, illustrating that the dissolution rate decreases significantly once the majority of RIS has been dissolved. In contrast, plot 804 shows a much shallower gradient at the left hand side of FIG. 8B, indicating a much lower initial dissolution rate of RIS. Plot 804 shows that approximately 10% of the as received RIS is dissolved within 10 minutes. In addition, the gradient of plot 804 is maintained as time increases. Plot 804 clearly shows that after approximately 60 minutes, less than 40% of the RIS is dissolved.

FIG. 8C shows three plots 807, 808, 809 of RIS dissolution percentage as a function of time. Plot 807 shows data for KET as received. Plot 808 shows data for MCC carrier particles coated with KET nanoparticles at a loading of 10 wt. %. Plot 809 shows data for MCC carrier particles coated with KET nanoparticles at a loading of 20 wt. %.

Similar to plots 802, 803 in FIG. 8A and plots 805, 806 in FIG. 8B, plots 808 and 809 show a higher dissolution rate of KET when loaded onto MCC carrier particles as a homogeneous coating of nanoparticles than its as received form. It can clearly be seen in FIG. 8C that both plots 808 and 809 exhibit a very steep gradient at the left-hand side of FIG. 8C, indicating a very high initial dissolution rate of KET. Plot 808 shows that substantially 85% of KET loaded onto the MCC carrier particles is dissolved within 10 minutes whilst plot 806 shows that substantially 90% of KET is dissolved within 10 minutes. The gradient of plots 808 and 809 then becomes much flatter as time increases, illustrating that the dissolution rate decreases significantly once the majority of KET has been dissolved. In contrast, plot 807 shows a shallower gradient at the left hand side of FIG. 8C, indicating a lower initial dissolution rate of KET. Plot 804 shows that approximately 60% of the as received RIS is dissolved within 10 minutes. The dissolution profile shown in plot 807 is similar to the plots 808, 809, but with a lower rate of dissolution. FIG. 8C clearly illustrates the improved dissolution performance of KET when loaded onto MCC carrier particles as a homogeneous coating of nanoparticles.

It is evident from FIGS. 8A to 8C that providing a homogeneous coating of API nanoparticles on carrier particles significantly enhances the dissolution performance of the API material. Providing APIs in such a form may improve the bioavailability of the API, and may enhance effectiveness of the API.

FIGS. 9, 10 and 11 show experimental results relating to mechanical properties of example tablets, formed from API nanoparticle coated MCC carrier particles formed using the method 200 described above.

Figure 9A:
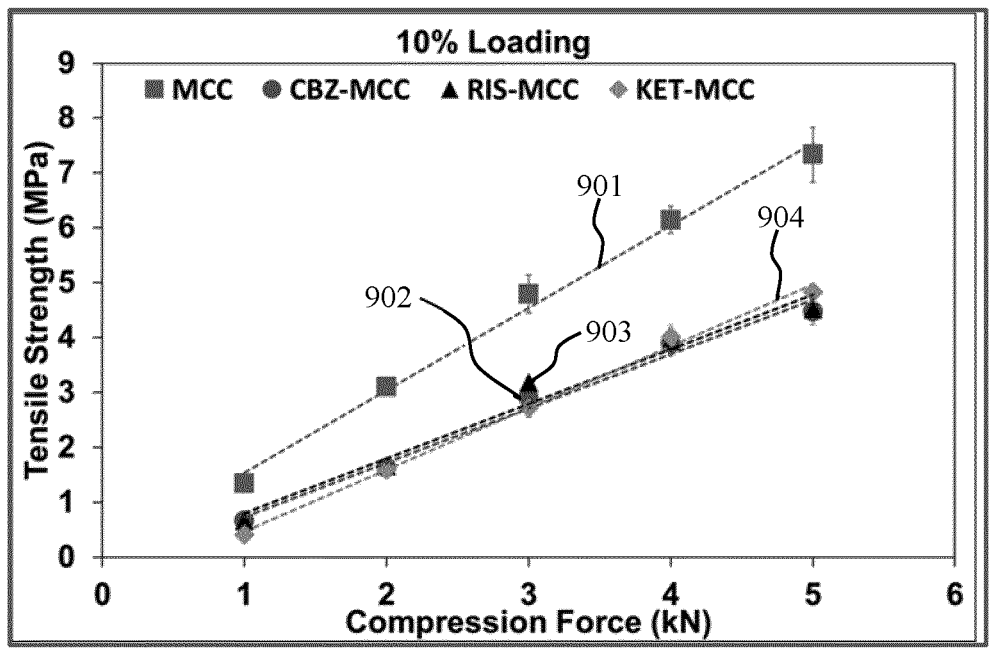
FIGS. 9A and 9B show plots of tablet tensile strength as a function of compaction force for the nanoparticle coated carrier particles produced by the method shown in FIG. 2.
Figure 9B:
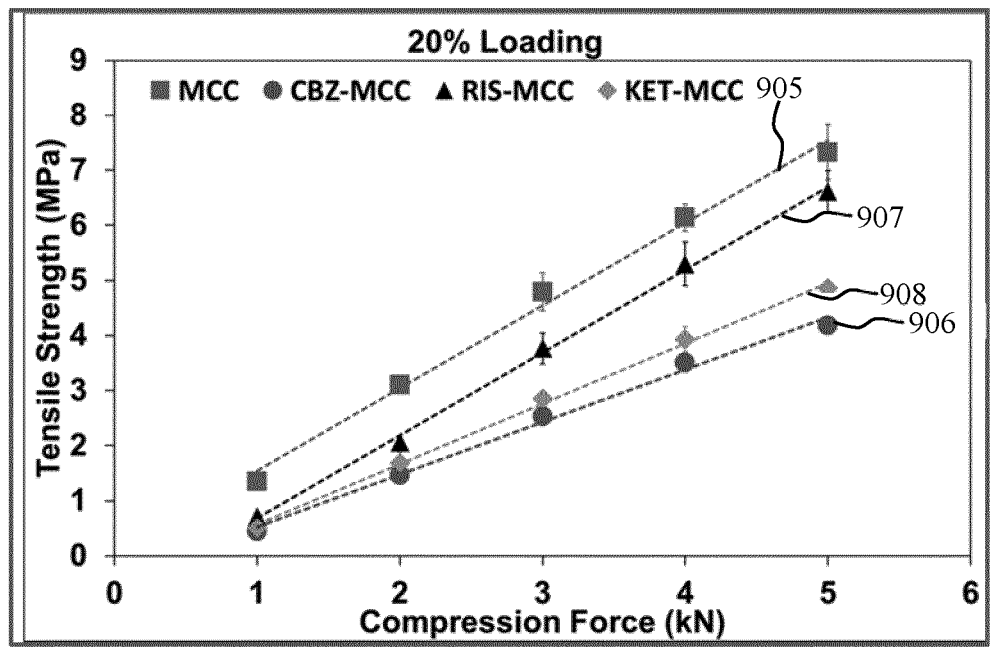

FIGS. 9A and 9B show plots of tensile strength of tablets of nanoparticle coated MCC carrier particles as a function of compaction force. In the embodiment shown, the tablets were formed using approximately 100 mg of uncoated or nanoparticle coated MCC carrier particles. In the embodiment shown, a Gamlen R-series compaction simulator with a flat-face 6 mm cylindrical punch and die was used to form the tablets, utilising a punch speed of 60 mm/min and graph sampling rate of 20 Hz. The plots show the tabletability profiles of the nanoparticle coated MCC carrier particles. Tabletability is considered to be the ability of a power to be compressed into a tablet at a specific tensile strength. Tensile strength of the tablets was calculated using the Fell-Newton equation as shown in Equation 5 below.

$$\sigma = \frac{2F}{\pi Dt} \quad \text{Equation 5}$$

σ is the tensile strength of the tablet, F is the tablet diametrical breaking force in N, D is the diameter of the tablet and t is the thickness of the tablet.

FIG. 9A shows four plots 901, 902, 903, 904. Plot 901 shows a tabletability profile for uncoated MCC carrier particles. Plot 902 shows a tabletability profile for MCC carrier particles coated with CBZ nanoparticles at a loading of 10 wt. %. Plot 903 shows a tabletability profile for MCC carrier particles coated with RIS nanoparticles at a loading of 10 wt. %. Plot 904 shows a tabletability profile for MCC carrier particles coated with KET nanoparticles at a loading of 10 wt. %.

FIG. 9B shows four plots 905, 906, 907, 908. Plot 905 shows a tabletability profile for uncoated MCC carrier particles. Plot 906 shows a tabletability profile for MCC carrier particles coated with CBZ nanoparticles at a loading of 20 wt. %. Plot 907 shows a tabletability profile for MCC carrier particles coated with RIS nanoparticles at a loading of 20 wt. %. Plot 908 shows a tabletability profile for MCC carrier particles coated with KET nanoparticles at a loading of 20 wt. %.

The tensile strength of all samples in plots 901 to 908 increases linearly with an increase in compaction force. Uncoated MCC carrier particles exhibit the highest tensile strength at a compaction force of 5 kN as shown in plots 901, 905. The tensile strength of each of the nanoparticle coated MCC carrier particle samples is approximately half or greater than that of the uncoated MCC carrier particles, as shown in plots 902, 903, 904, 906, 907, 908. MCC is an easily compressible material with excellent tensile strength that has been extensively studied and reported in literature. Though the tensile strength of the nanoparticle coated MCC carrier particles is lower than that of the uncoated MCC carrier particles, the tensile strength of the nanoparticle coated MCC carrier particles is above 2 MPa at compression forces of 4 kN and higher, for each of CBZ, RIS and KET nanoparticle coated MCC carrier particles. A tensile strength of 2 MPa or greater is an essential requirement of tablets for acceptable manufacturability, quality and biopharmaceutical performance.

A tabletability parameter, $C_p$, was obtained for each sample using linear regression for each of plots 901 to 904. The linear correlation between tensile strength and compaction pressure is shown in equation 6 below.

$$\sigma_t = C_p P + b \quad \text{Equation 6}$$

$\sigma_t$ is the tensile strength of the tablet, $C_p$ is the tabletability parameter, P is the compaction pressure and b is a constant.

The gradient of each of plots 901 to 904 is therefore indicative of the tabletability parameter $C_p$. As shown in Table 4 below, uncoated MCC carrier particles exhibit the highest value of $C_p$ at 1.5. The nanoparticle coated MCC carrier particles at both 10 wt. % loading and 2 wt. % loading exhibit $C_p$ values close to 1.0.

Figure 10A:
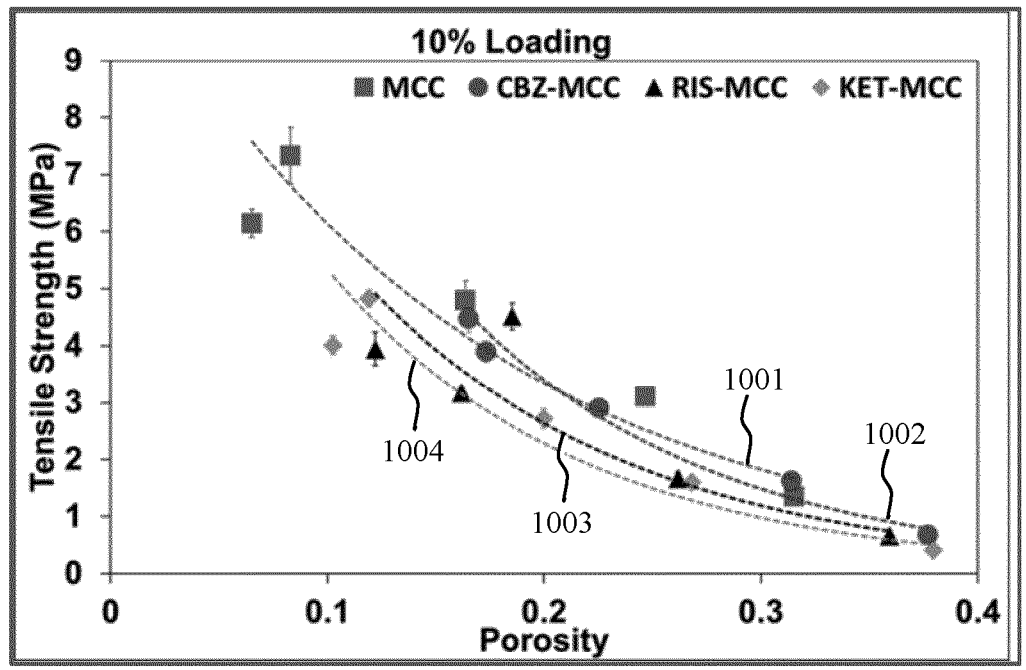
FIGS. 10A and 10B show plots of tablet tensile strength as a function of porosity for the nanoparticle coated carrier particles produced by the method shown in FIG. 2.
Figure 10B:
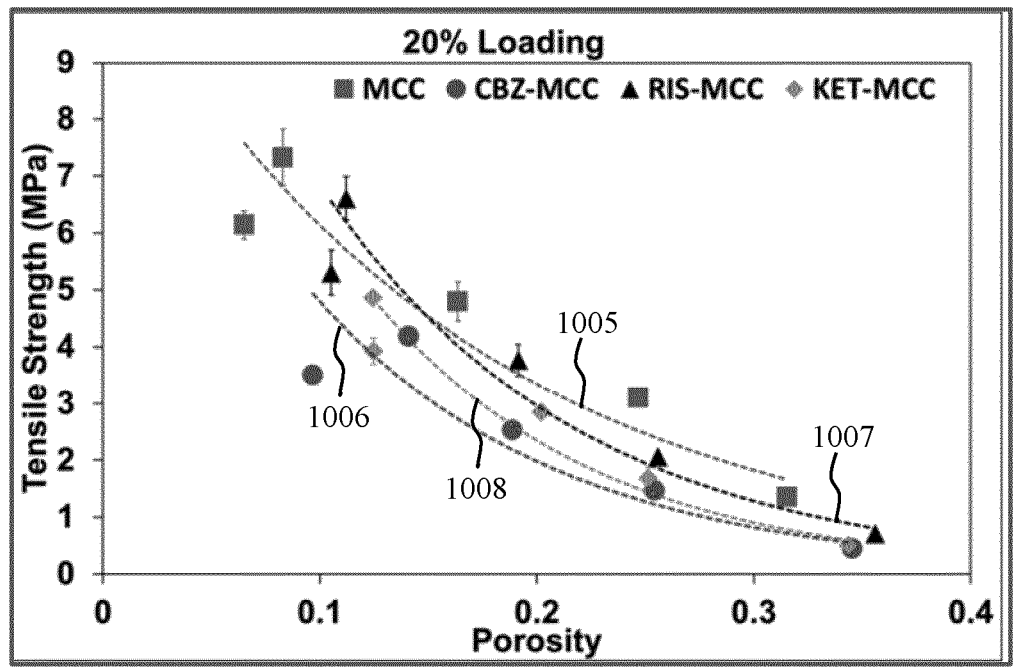

FIGS. 10A and 10B show plots of tensile strength of tablets of nanoparticle coated MCC carrier particles as a function of porosity. The plots show the compactability profiles of the nanoparticle coated MCC carrier particles. Compactibility of a powder relates the plastic deformation of a powder with its ability to reduce volume under applied pressure. The Ryshkewitch-Duckworth equation is used to analyse the compactibility of all samples, with the fitted parameters shown in Table 4 below. The Ryshkewitch-Duckworth equation is shown below in Equation 7.

$$\sigma_t = \sigma_{t0} e^{-bP} \quad \text{Equation 7}$$

$\sigma_t$ is the tablet tensile strength in MPa, $\sigma_{t0}$ is the tablet tensile strength in MPa at zero porosity, P is tablet porosity and b is an empirical constant representing bonding capacity (where higher b represents stronger bonding capacity of particles).

Tablet porosity was calculated using equation 8 shown below.

$$\text{Tablet porosity} = 1 - \frac{\rho_{app}}{\rho_{true}} \quad \text{Equation 8}$$

$\rho_{app}$ is apparent density, and $\rho_{true}$ is true density. Apparent density is calculated by dividing the weight of each tablet by its volume (determined by measuring the dimensions of the tablet).

True density was measured at ambient temperature, by dividing the mass of the tablet divided by the volume of the tablet excluding open and closed pores. In the embodiment shown, the true density is measured using an Accupyc II gas displacement pycnometry system, based on US699 standard procedure. Helium is purged into the sample chamber to determine tablet volume.

FIG. 10A shows four plots 1001, 1002, 1003, 1004. Plot 1001 shows a compactability profile for uncoated MCC carrier particles. Plot 1002 shows a compactability profile for MCC carrier particles coated with CBZ nanoparticles at a loading of 10 wt. %. Plot 1003 shows a compactability profile for MCC carrier particles coated with RIS nanoparticles at a loading of 10 wt. %. Plot 1004 shows a compactability profile for MCC carrier particles coated with KET nanoparticles at a loading of 10 wt. %.

FIG. 10B shows four plots 1005, 1006, 1007, 1008. Plot 1005 shows a compactability profile for uncoated MCC carrier particles. Plot 1006 shows a compactability profile for MCC carrier particles coated with CBZ nanoparticles at a loading of 20 wt. %. Plot 1007 shows a compactability profile for MCC carrier particles coated with RIS nanoparticles at a loading of 20 wt. %. Plot 1008 shows a compactability profile for MCC carrier particles coated with KET nanoparticles at a loading of 20 wt. %.

The tensile strength at zero porosity for all nanoparticle coated MCC carrier particles (shown in plots 1002 to 1004 and 1006 to 1008) is higher than that of uncoated MCC carrier particles (shown in plots 1001 and 1005). The only exception is MCC carrier particles coated with KET nanoparticles at a loading of 10 wt. % (plot 1004), where the tensile strength at zero porosity is 8.48. That could potentially be due to larger nanoparticle sizes agglomerated together, thereby introducing larger porosity to the system.

Moreover, a higher b value is an indication of bonding capacity, representing a stronger bonding between the primary particles. Uncoated MCC carrier particles exhibit the lowest b value compared to the nanoparticle coated MCC carrier particles at loadings of both 10 wt. % and 20 wt. %. That may correspond to a lower tendency of the uncoated MCC carrier particles to interact with each other. On the contrary, a homogeneous nanoparticle coating on MCC carrier particles may increase cohesive interactions between the MCC carrier particles, leading to a higher b value.

That is also supported by the SEM micrographs in FIGS. 6A to 6C, which show a uniform coverage of API nanoparticles on the MCC carrier particles.

plasticity and high compressibility based on its high Heckel coefficient k and low yield pressure $P_y$. On the contrary, nanoparticle coated MCC carrier particles at loading of 10 wt. % exhibit inverse behaviour to that of uncoated MCC carrier particles, due to low Heckel coefficients k and high yield pressures $P_y$. Nanoparticle coated MCC carrier particles at loading of 20 wt. % present increased compressibility relative to nanoparticle coated MCC carrier particles at loading of 10 wt. %, but do not exhibit compressibility as efficient as that of uncoated MCC carrier particles.

TABLE 4

Results of tabletability, compactability and compressibility for talets formed from uncoated MCC carrier particles, nanoparticle coated MCC carrier particles at loading of 10 wt. % and nanoparticle coated MCC carrier particles at loading of 20 wt. %. $C_p$ is tabletability parameter, $\sigma_{t0}$ is tablet tensile strength at zero porosity, b is an empirical constant, k is the Heckel coefficient, $P_y$ is yield pressure.

| Loading | Sample | Tabletability | | Compactability | | | Compressibility | | |
|---|---|---|---|---|---|---|---|---|---|
| | | $C_p$ | $R^2$ | $\sigma_{t0}$/MPa | −b | $R^2$ | k | $P_y$/kN | $R^2$ |
| | MCC | 1.5 | 0.99 | 11.25 | 6.1 | 0.91 | 0.42 | 2.36 | 0.87 |
| | CBZ | 0.99 | 0.99 | 17.88 | 8.3 | 0.97 | 0.23 | 4.37 | 0.97 |
| | RIS | 1.0 | 0.97 | 12.96 | 7.9 | 0.90 | 0.21 | 4.74 | 0.62 |
| | KET | 1.1 | 0.99 | 8.48 | 8.5 | 0.95 | 0.33 | 3.02 | 0.91 |
| | CBZ | 1.02 | 0.99 | 11.58 | 8.8 | 0.92 | 0.28 | 3.58 | 0.77 |
| | RIS | 1.5 | 0.99 | 15.84 | 8.4 | 0.97 | 0.34 | 2.97 | 0.93 |
| | KET | 1.1 | 0.99 | 15.97 | 9.6 | 0.96 | 0.30 | 3.35 | 0.96 |

Figure 11A:
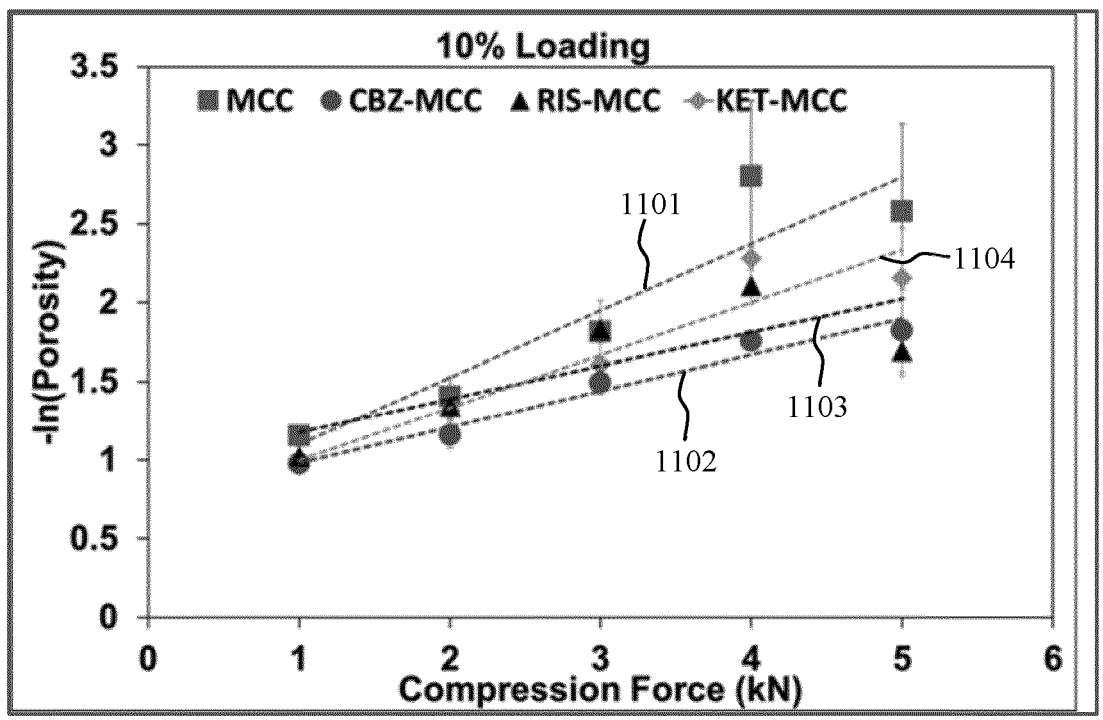
FIGS. 11A and 11B show plots of $-\ln$(porosity) of tablets as a function of compaction force for nanoparticle coated carrier particles produced by the method shown in FIG. 2.
Figure 11B:
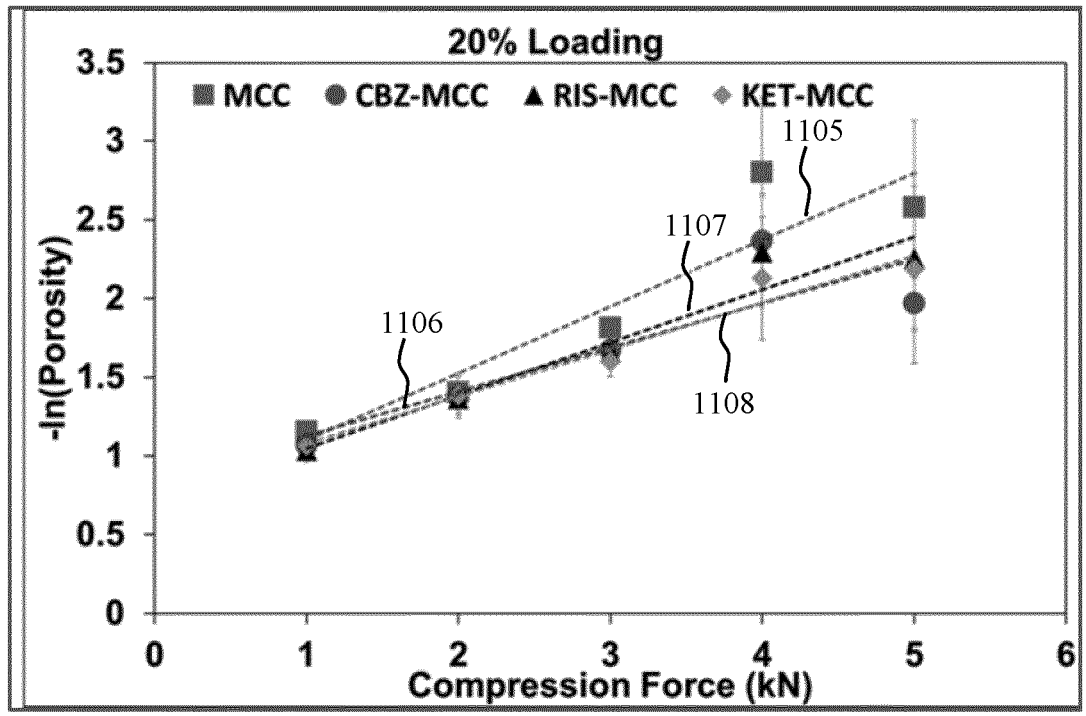

FIGS. 11A and 11B show plots of −ln(porosity) of tablets as a function of compaction force. The plots show the compressibility profiles of the nanoparticle coated MCC carrier particles. The Heckel equation is used to analyse the compressibility of all samples. The Heckel equation is shown below in Equation 9.

$$-\ln\varepsilon = \ln\left(\frac{1}{1-D}\right) = k.P + A \quad \text{Equation 9}$$

$\varepsilon$ is tablet density, D is relative density of the tablet, k is the Heckel coefficient, P is applied compression pressure and A is the intercept. The reciprocal of the Heckel coefficient is yield pressure, $P_y$. High k values and low $P_y$ values are indicative of more compressible samples.

FIG. 11A shows four plots 1101, 1102, 1103, 1104. Plot 1101 shows a compressibility profile for uncoated MCC carrier particles. Plot 1102 shows a compressibility profile for MCC carrier particles coated with CBZ nanoparticles at a loading of 10 wt. %. Plot 1103 shows a compressibility profile for MCC carrier particles coated with RIS nanoparticles at a loading of 10 wt. %. Plot 1104 shows a compressibility profile for MCC carrier particles coated with KET nanoparticles at a loading of 10 wt. %.

FIG. 11B shows four plots 1105, 1106, 1107, 1108. Plot 1105 shows a compressibility profile for uncoated MCC carrier particles. Plot 1106 shows a compressibility profile for MCC carrier particles coated with CBZ nanoparticles at a loading of 20 wt. %. Plot 1107 shows a compressibility profile for MCC carrier particles coated with RIS nanoparticles at a loading of 20 wt. %. Plot 1108 shows a compressibility profile for MCC carrier particles coated with KET nanoparticles at a loading of 20 wt. %.

The Heckel coefficient k (slope of the plot) and yield pressure $P_y$ for each of plots 1101 to 1108 are shown in Table 4 below. Uncoated MCC carrier particles exhibit good FIGS. 9, 10 and 11 illustrate tablet mechanical properties (tabletability, compactability and compressibility) that confirm the improved, optimal rheological properties of API nanoparticle coated carrier particles produced by the method of the present invention. FIGS. 9, 10 and 11 therefore also clearly illustrate that such API nanoparticle coated carrier particles can be used to produce tablets having improved manufacturability, quality and biopharmaceutical performance.

Figure 12:
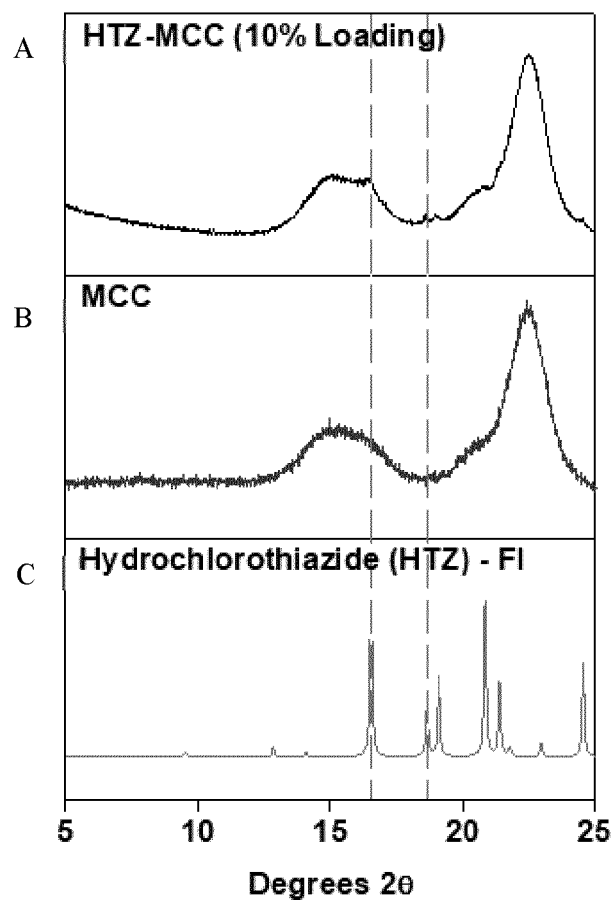
FIG. 12 shows X-ray diffraction (XRD) patterns for other nanoparticle coated carrier particles produced by the method shown in FIG. 2.
Figure 13:
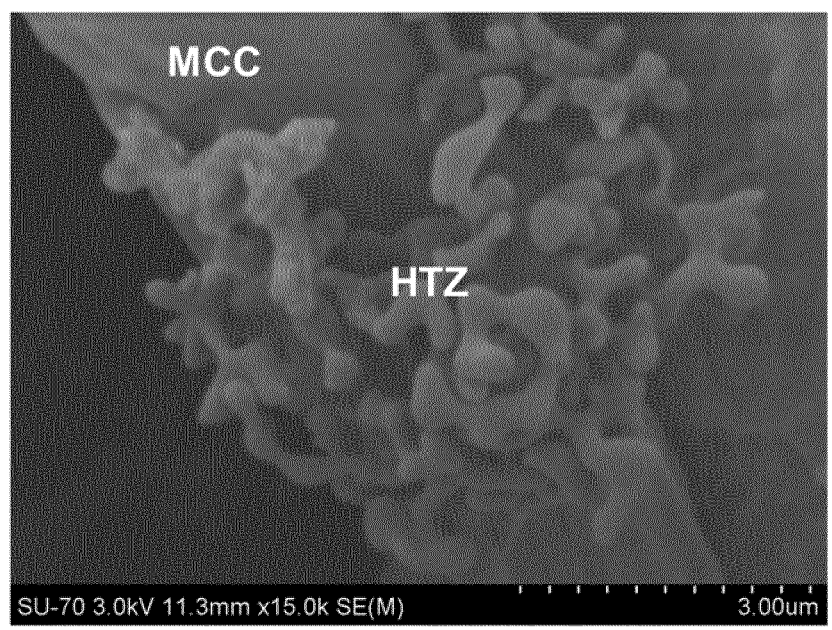
FIG. 13 shows a scanning electron microscope (SEM) micrograph of the nanoparticle coated carrier particles of FIG. 12.

Table 5 and FIGS. 12 and 13 show further experimental results obtained for another example produced using the method 200 described above. In the example shown, API nanoparticles of hydrochlorothiazide (HTZ) were coated onto excipient carrier particles formed from microcrystalline cellulose (MCC). HTZ is a class IV API (according to the BCS) whilst CBZ, RIS and KET described above are class II APIs. Nevertheless, the data shown in Table 5 and FIGS. 12 and 13 shows that the method of the present disclosure is applicable to producing nanoparticle coatings on excipient carrier particles using APIs from different classes (according to the BCS), as well as more generally applicable to producing particle coatings using supercritical fluids.

TABLE 5

Results of API nanoparticle size, polymorphism and process yield obtained using the method 200 to coat excipient carrier particles of microcrystalline cellulose with API nanoparticles of hydrochlorothiazide at 10% loading (see Equation 2 above).

| API | Run No. | Size/nm | Polymorphism | Yield/% |
|---|---|---|---|---|
| Hydrochlorothiazide | 1 | 595 ± 171 | FI | 76 ± 2 |
| | 2 | 3436 ± 79 | FI | 71 ± 4 |

The results shown in Table 5 were obtained using an API concentration of substantially 10 mg·mL$^{-1}$, a supercritical carbon dioxide pressure of substantially 10 MPa, and an API flow rate of substantially 0.4 mL·min$^{-1}$. The API concentration used results in the formation of a saturated solution as discussed above. As can be seen from the results set out in Table 5, the API nanoparticle size produced in the examples shown is between substantially 300 nm and substantially 600 nm. The process yield in the examples shown is between substantially 70% and substantially 80%, where the yield is defined as shown in Equation 1 above.

FIG. 12 shows X-ray diffraction (XRD) patterns obtained for the coated carrier particles of Table 5. FIG. 12 is discussed in further detail below.

FIG. 12A shows an XRD pattern obtained for MCC carrier particles coated with HTZ nanoparticles at 10 wt. % loading. FIG. 12B shows an XRD pattern for MCC without HTZ nanoparticles. FIG. 12C shows an XRD pattern for the HTZ polymorph FI.

A location of some dominant peaks on the XRD pattern of FIG. 12C is mapped onto the XRD patterns of FIGS. 12A, using the dashed lines running across each of FIGS. 12A to 12C. It can be seen that locations of the peaks in the XRD pattern of FIG. 12C directly correspond to locations of peaks in the XRD pattern of FIG. 12A. By visual comparison of FIGS. 12A, 12B and 12C, it is evident that the XRD patterns of FIG. 12A show the XRD pattern for MCC superimposed with the XRD pattern for the HTZ FI polymorph. That indicates that the polymorphic form of HTZ nanoparticles coated onto the MCC carrier particles is the stable FI form, confirming that the method 200 may produce crystalline nanoparticles at suitable concentrations (concentrations forming a saturated solution as discussed above).

FIG. 13 shows a scanning electron microscope (SEM) micrograph of the coated carrier particles of Table 5. FIG. 13 shows a SEM micrograph of MCC carrier particles coated with HTZ nanoparticles at 10 wt. % loading. The micrograph has a magnification of ×15000, and a scale bar showing 3.00 μm is included at the bottom right hand corner of FIG. 13. An accelerating voltage of 3.0 kV was used at a working distance of 11.3 mm.

In FIG. 13, the darker, continuous regions of the micrographs indicate MCC, whilst the lighter, discontinuous (i.e., particulate) regions indicate HTZ nanoparticles, as shown by the annotations MCC and HTZ respectively. The distribution of the lighter regions in FIG. 13 illustrates that the method 200 results in a homogeneous coating of HTZ nanoparticles on the MCC carrier particles. FIG. 13 shows that the HTZ nanoparticles are coated onto the MCC carrier particles substantially individually. The HTZ nanoparticles can be distinguished and seen distinctly from one another.

FIG. 13 further demonstrates that the method 200 results in a homogeneous coating of API nanoparticles on the MCC carrier particles, irrespective of the class (according to the BCS) that the API belongs to. The precipitated API nanoparticles may be captured on the surface of the MCC carrier particles individually before agglomerating. The average size and standard deviation of the API nanoparticles was also determined from the SEM micrographs, using a minimum of 150 nanoparticles for each sample.

Whilst aspects and embodiments are generally described with respect to nanoparticles and using supercritical carbon dioxide, it will be apparent to the skilled person that the above teaching is more generally applicable to particle production using supercritical fluids.

From reading the present disclosure, other variations and modifications will be apparent to the skilled person. Such variations and modifications may involve equivalent and other features which are already known in the art of particle coating, and which may be used instead of, or in addition to, features already described herein.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable sub-combination. The applicant hereby gives notice that new claims may be formulated to such features and/or combinations of such features during the prosecution of the present application or of any further application derived therefrom. Features of the devices and systems described may be incorporated into/used in corresponding methods. Where features are disclosed in connection with one embodiment of a particle coating method, it should be appreciated that any one or more or all of the same features may be incorporated in other embodiments of particle coating methods, instead of or in addition to the features described for the particular embodiment. That is, any and all combinations of features are envisaged, and are envisaged to be interchangeable, replaceable, added or removed.

For the sake of completeness, it is also stated that the term "comprising" does not exclude other elements or steps, the term "a" or "an" does not exclude a plurality, a single processor or other unit may fulfil the functions of several means recited in the claims and any reference signs in the claims shall not be construed as limiting the scope of the claims.

The invention claimed is:

1. A method of producing a particle coating on one or more items, the method comprising:
mixing a supercritical fluid with a solution comprising dissolved material for forming particles;
spraying the mixture into a precipitation chamber to precipitate particles, wherein the chamber is at a pressure below a supercritical pressure of the supercritical fluid;
capturing the precipitated particles on one or more items located within the chamber;
introducing a flow of drying gas into the chamber; and
directing the flow of drying gas from a top portion of the chamber towards the one or more items.

2. The method of claim 1, comprising orienting a flow direction of drying gas and a spray direction of the mixture in substantially the same direction.

3. The method of claim 1, comprising spraying the mixture through a nozzle into the chamber to precipitate particles, and optionally wherein a nozzle orifice size of the nozzle is substantially 150 um or smaller.

4. The method of claim 1, comprising capturing the precipitated particles on carrier particles in a fluidized bed located within the chamber.

5. The method of claim 4, comprising fluidizing the bed of carrier particles using the flow of drying gas.

6. The method of claim 4, wherein the carrier particles comprise microcrystalline cellulose.

7. The method of claim 1, wherein the solution comprises an active pharmaceutical ingredient dissolved in an organic solvent, and optionally wherein:
   i) the active pharmaceutical ingredient comprises one of carbamazepine, risperidone, ketoprofen and hydrochlorothiazide; and/or
   ii) the organic solvent comprises an alcohol, and optionally wherein the alcohol is methanol.

8. The method of claim 1, wherein a distance between an entry location of the spray and the one or more items is between substantially 10 cm and substantially 20 cm.

9. The method of claim 1, wherein the solution comprises a saturated solution.

10. The method of claim 1, comprising controlling a concentration of the solution to control particle loading on the one or more items.

11. The method of claim 1, further comprising supporting the one or more items on a surface configured to allow fluid to pass through, and optionally wherein the surface comprises a mesh.

12. The method of claim 11, further comprising selecting or controlling an area of the surface configured to allow fluid to pass through, and optionally by controlling movement of a cover disposed over the surface.

13. The method of claim 1, wherein the method comprises mixing the supercritical carbon dioxide with the solution in a nozzle, and/or wherein the nozzle comprises a coaxial nozzle.

14. A method of producing particles, comprising:
   mixing a supercritical fluid with a solution comprising dissolved material for forming particles;
   spraying the mixture into a precipitation chamber to precipitate particles, wherein the chamber is at a pressure below a supercritical pressure of the supercritical fluid;
   introducing a flow of drying gas into the chamber; and
   directing the flow of drying gas from a top portion of the chamber.

15. An apparatus for producing a particle coating on one or more items, the apparatus comprising:
   a chamber;
   a surface configured to support one or more items to be coated within the chamber; and
   a nozzle;
      wherein the nozzle is configured to spray a mixture of a supercritical fluid and a solution comprising dissolved material for forming particles into the chamber; and
      the chamber is configured to be held at a pressure below a supercritical pressure of the supercritical fluid; and
   an inlet configured to introduce a flow of drying gas into the chamber, wherein the inlet is further configured to direct the flow of drying gas from a top portion of the chamber towards the one or more items.

16. The apparatus of claim 15, wherein the surface is operable within the chamber between a first configuration and a second configuration.

17. The apparatus of claim 16, wherein:
   in the first configuration, the surface is configured to support the one or more items for coating; and
   in the second configuration, the surface is configured to direct or allow coated items to travel towards an outlet of the chamber.

18. The apparatus of claim 15, wherein the surface comprises one or more apertures or perforations configured to allow fluid to pass through the surface.

* * * * *